(12) United States Patent
Duplessis et al.

(10) Patent No.: US 12,209,091 B2
(45) Date of Patent: Jan. 28, 2025

(54) ISOINDOLINONE DERIVATIVES AS SELECTIVE ALLOSTERIC INHIBITORS OF EGFR MUTANT CANCERS

(71) Applicant: Hoffmann-La Roche Inc., Little Falls, NJ (US)

(72) Inventors: Martin Duplessis, Somerville, MA (US); Annick Goergler, Colmar (FR); Georg Jaeschke, Basel (CH); Buelent Kocer, Maulburg (DE); Bernd Kuhn, Reinach BL (CH); Kiel Lazarski, Boston, MA (US); Yanke Liang, Belmont, MA (US); Yvonne Alice Nagel, Basel (CH); Ulrike Obst Sander, Reinach BL (CH); Antonio Ricci, Biel-Benken (CH); Daniel Rueher, Raedersdorf (FR); Sandra Steiner, Sursee (CH)

(73) Assignee: Hoffmann-La Roche Inc., Little Falls, NJ (US)

( * ) Notice: Subject to any disclaimer, the term of this patent is extended or adjusted under 35 U.S.C. 154(b) by 674 days.

(21) Appl. No.: 17/105,060

(22) Filed: Nov. 25, 2020

(65) Prior Publication Data

US 2021/0079005 A1    Mar. 18, 2021

Related U.S. Application Data

(63) Continuation of application No. PCT/EP2019/067111, filed on Jun. 27, 2019.

(30) Foreign Application Priority Data

Jun. 29, 2018  (EP) .................................. 18180758

(51) Int. Cl.
| | | |
|---|---|---|
| C07D 487/04 | (2006.01) | |
| A61K 9/00 | (2006.01) | |
| A61K 9/02 | (2006.01) | |
| A61K 9/08 | (2006.01) | |
| A61K 9/20 | (2006.01) | |
| A61K 9/48 | (2006.01) | |
| A61K 47/02 | (2006.01) | |
| A61K 47/12 | (2006.01) | |
| A61K 47/26 | (2006.01) | |
| A61K 47/32 | (2006.01) | |
| A61K 47/34 | (2017.01) | |
| A61K 47/38 | (2006.01) | |

(52) U.S. Cl.
CPC .......... *C07D 487/04* (2013.01); *A61K 9/0019* (2013.01); *A61K 9/02* (2013.01); *A61K 9/08* (2013.01); *A61K 9/2009* (2013.01); *A61K 9/2018* (2013.01); *A61K 9/2054* (2013.01); *A61K 9/4825* (2013.01); *A61K 9/485* (2013.01); *A61K 9/4858* (2013.01); *A61K 9/4866* (2013.01); *A61K 9/4875* (2013.01); *A61K 47/02* (2013.01); *A61K 47/12* (2013.01); *A61K 47/26* (2013.01); *A61K 47/32* (2013.01); *A61K 47/34* (2013.01); *A61K 47/38* (2013.01)

(58) Field of Classification Search
CPC ..... C07D 471/14; C07D 487/04; A61P 35/00; A61K 9/00; A61K 31/496
See application file for complete search history.

(56) References Cited

U.S. PATENT DOCUMENTS

2011/0212078 A1    9/2011  Reddy et al.

FOREIGN PATENT DOCUMENTS

| CN | 102060848 A | 5/2011 |
|---|---|---|
| CN | 102093339 A | 6/2011 |
| WO | WO 2007/143434 A2 | 12/2007 |
| WO | WO 2009/158369 A1 | 12/2009 |
| WO | WO 2011/100380 A1 | 8/2011 |
| WO | WO 2011/128279 A1 | 10/2011 |
| WO | WO 2016/183534 A1 | 11/2016 |
| WO | WO 2017/004383 A1 | 1/2017 |
| WO | WO 2018/115218 A1 | 6/2018 |
| WO | WO 2018/220149 A1 | 12/2018 |

OTHER PUBLICATIONS

Wermuth, Molecular variations based in isosteric replacements, The Practice of Medicinal Chemistry, 1996, 203-237 (Year: 1996).*
U.S. Pat. No. 10,882,848, B2, U.S. Appl. No. 16/449,040, Duplessis et al, filed Jan. 5, 2021.
U.S. Pat. No. 11,117,890, B2, U.S. Appl. No. 16/700,900, Jaeschke et al, filed Sep. 14, 2021.
2021/0070739, A1, U.S. Appl. No. 17/103,648, Duplessis et al, filed Mar. 11, 2021.
2022/0112199, A1, U.S. Appl. No. 17/558,108, Dolente et al., filed Apr. 14, 2022.
2022/0135571, A1, U.S. Appl. No. 17/558,053, Dolente et al., filed May 5, 2022.
U.S. Appl. No. 17/558,053, Dolente et al., filed Dec. 21, 2021.
U.S. Appl. No. 17/558,108, Dolente et al., filed Dec. 21, 2021.
Dyson G., et al. "Chemistry of synthetic medicinal substances" translated from English. Moscow, "Mir", 1964, pp. 12-19.
Cheng Y and W H Prusoff, "Relationship between the inhibition constant (K1) and the concentra+G2:H9tion of inhibitor which causes 50 per cent inhibition (150) of an enzymatic reaction", Biochem Pharmacol., Dec. 1, 1973, 22(23):3099-108. doi:10.1016/0006-2952(73)90196-2.
Ciardiello, F., and Tortora, G., "EGFR antagonists in cancer treatment", The New England journal of medicine, 2008, 358, 1160-1174.
International Search Report and Written Opinion for PCT/EP2019/067111 mailed Jan. 2, 2020.

(Continued)

*Primary Examiner* — Kortney L. Klinkel
*Assistant Examiner* — Padmaja S Rao
(74) *Attorney, Agent, or Firm* — Knowles Intellectual Property Strategies, LLC

(57) ABSTRACT

The present invention provides compounds which are selective allosteric inhibitors of T790M/L858R, T790M/L858R/C797S, L858R, L858R/C797S containing EGFR mutants, their manufacture, pharmaceutical compositions containing them and their use as therapeutically active substances.

30 Claims, No Drawings

(56) References Cited

OTHER PUBLICATIONS

Jia et al., "Overcoming EGFR(T790M) and EGFR(C797S) resistance with mutant-selective allosteric inhibitors", Nature, Jun. 2016, 534, 129-132.

Li H Q et al., "Synthesis and structure-activity relationships of N-benzyl-N-(X-2-hydroxybenzyl)-N-phenylureas and thioureas as antitumor agents", Bioorganic and Medicinal Chemistry, 2010, 18(1), 305-313, XP026810721.

Lu et al., "Targeting EGFR $^{L858R/T790M}$ and EGFR$^{L858R/T790M/C797S}$ resistance mutations in NSCLC: Current developments in medicinal chemistry", Med Res Rev., 2018; 1-32; https://doi.org/10.1002/med.21488.

Paez, J. et al., "EGFR mutations in lung cancer: correlation with clinical response to gefitinib therapy", Science, 2004, 304, 1497-1500.

Sharma SV, Bell DW, Settleman J, Haber DA., "Epidermal growth factor receptor mutations in lung cancer", Nat Rev Cancer, Mar. 2007, 7(3), 169-81.

Thress, K. S. et al., "Acquired EGFR C797S mutation mediates resistance to AZD9291 in non-small cell lung cancer harboring EGFR T790M", Nat. Med., 2015, 21, 560-562.

Wang et al., "EGFR C797S mutation mediates resistance to third-generation inhibitors in T790M-positive non-small cell lung cancer", J Hematol Oncol., 2016, 9, 59.

Yang et al., "Investigating Novel Resistance Mechanisms to Third-Generation EGFR Tyrosine Kinase Inhibitor Osimertinib in Non-Small Cell Lung Cancer Patients", Clinical Cancer Research, DOI: 10.1158/1078-0432.CCR-17-2310.

Yarden, Y., Sliwkowski, MX, "Untangling the ErbB signalling network", Nature Review Mol Cell Biol., Feb. 2001, 2(2), 127-37.

* cited by examiner

ISOINDOLINONE DERIVATIVES AS SELECTIVE ALLOSTERIC INHIBITORS OF EGFR MUTANT CANCERS

CROSS-REFERENCED TO RELATED APPLICATIONS

This application is a continuation of International Application No. PCT/EP2019/067111, filed in the European Receiving Office on Jun. 27, 2019, which claims the benefit of European Patent Application 18180758.7, filed Jun. 29, 2018. The entirety of these applications are hereby incorporated by reference herein for all purposes.

FIELD OF THE INVENTION

The present invention provides compounds which are selective allosteric inhibitors of T790M/L858R, T790M/L858R/C797S, L858R, L858R/C797S containing EGFR mutants, their manufacture, pharmaceutical compositions containing them and their use as therapeutically active substances.

BACKGROUND OF THE INVENTION

The HER family receptor tyrosine kinases are mediators of cell growth, differentiation and survival. The receptor family includes four distinct members, i.e. epidermal growth factor receptor (EGFR, ErbB1, or HER1) HER2 (ErbB2), HER3 (ErbB3) and HER4 (ErbB4). Upon ligand binding the receptors form homo and heterodimers and subsequent activation of the intrinsic tyrosine kinase activity leads to receptor auto-phosphorylation and the activation of downstream signaling molecules (Yarden, Y., Sliwkowski, MX. Untangling the ErbB signalling network. Nature Review Mol Cell Biol. 2001 February; 2(2): 127-37). De-regulation of EGFR by overexpression or mutation has been implicated in many types of human cancer including colorectal, pancreatic, gliomas, head and neck and lung cancer, in particular non-small cell lung cancer (NSCLC) and several EGFR targeting agents have been developed over the years (Ciardiello, F., and Tortora, G. (2008). EGFR antagonists in cancer treatment. The New England journal of medicine 358, 1160-1174). Erlotinib (Tarceva®), a reversible inhibitor of the EGFR tyrosine kinase was approved in numerous countries for the treatment of recurrent NSCLC.

An impressive single agent activity of EGFR tyrosine kinase inhibitors is observed in a subset of NSCLC patients whose tumors harbor somatic kinase domain mutations, whereas clinical benefit in wild-type EGFR patients is greatly diminished (Paez, J. et al. (2004). EGFR mutations in lung cancer: correlation with clinical response to gefitinib therapy. Science (New York, NY 304, 1497-1500). The most common somatic mutations of EGFR are exon 19 deletions with delta 746-750 the most prevalent mutation and the exon 21 amino acid substitutions with L858R the most frequent mutation (Sharma S V, Bell D W, Settleman J, Haber D A. Epidermal growth factor receptor mutations in lung cancer. Nat Rev Cancer. 2007 March; 7(3): 169-81).

Treatment resistance arises frequently, often due to the secondary T790M mutation within the ATP site of the receptor. Some developed mutant-selective irreversible inhibitors are highly active against the T790M mutant, but their efficacy can be compromised by acquired mutation of C797S, that is the cysteine residue with which they form a key covalent bond (Thress, K. S. et al. Acquired EGFR C797S mutation mediates resistance to AZD9291 in non-small cell lung cancer harboring EGFR T790M. Nat. Med. 21, 560-562 (2015)). C797S mutation was further reported by Wang to be a major mechanism for resistance to T790M-targeting EGFR inhibitors (Wang et al. EGFR C797S mutation mediates resistance to third-generation inhibitors in T790M-positive non-small cell lung cancer, J Hematol Oncol. 2016; 9: 59). Additional mutations that cause resistance to Osimertinib are described by Yang, for example L718Q. (Yang et al, Investigating Novel Resistance Mechanisms to Third-Generation EGFR Tyrosine Kinase Inhibitor Osimertinib in Non-Small Cell Lung Cancer Patients, Clinical Cancer Research, DOI: 10.1158/1078-0432.CCR-17-2310) Lu et al. report in a review article on Targeting $EGFR^{L858R/T790M}$ and $EGFR^{L858R/T790M/C797S}$ resistance mutations in NSCLC treatment (Lu et al. Targeting $EGFR^{L858R/T790M}$ and $EGFR^{L858R/T790M/C797S}$ resistance mutations in NSCLC: Current developments in medicinal chemistry, Med Res Rev 2018; 1-32).

As most available EGFR tyrosine kinase inhibitors target the ATP-site of the kinase, there is a need for new therapeutic agents that work differently, for example through targeting drug-resistant EGFR mutants.

Recent studies suggest that purposefully targeting allosteric sites might lead to mutant-selective inhibitors (Jia et al. Overcoming EGFR(T790M) and EGFR(C797S) resistance with mutant-selective allosteric inhibitoRS, June 2016, Nature 534, 129-132)

There is just a need in the generation of selective molecules that specifically inhibit T790M/L858R, T790M/L858R/C797S, L858R, L858R/C797S containing EGFR mutants useful for the therapeutic and/or prophylactic treatment of cancer, in particular T790M and C797S containing EGFR mutants.

WO2009158369 describes certain heterocyclic antibacterial agents. WO2016183534 describes certain heterocyclic compounds suitable as EBNA1 inhibitors. WO2011128279 describes certain heterocyclic compounds suitable as mGluR5 modulators.

SUMMARY OF THE INVENTION

The present invention provides compounds of formula I, or a pharmaceutically acceptable salt thereof,

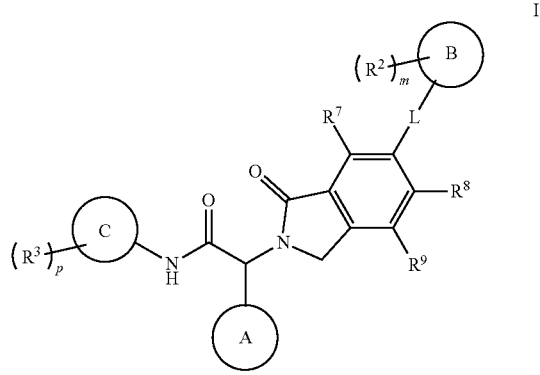

wherein the substituents and variables are as described below and in the claims, or a pharmaceutically acceptable salt thereof.

The present compounds are useful for the therapeutic and/or prophylactic treatment of cancer.

DETAILED DESCRIPTION OF THE INVENTION

The present invention provides a compound of formula I and their pharmaceutically acceptable salts thereof, the preparation of the above-mentioned compounds, medicaments containing them and their manufacture as well as the use of the above-mentioned compounds in the therapeutic and/or prophylactic treatment of cancer, in particular non-small-cell lung cancer.

The following definitions of the general terms used in the present description apply irrespectively of whether the terms in question appear alone or in combination with other groups.

Unless otherwise stated, the following terms used in this Application, including the specification and claims, have the definitions given below. It must be noted that, as used in the specification and the appended claims, the singular forms "a", "an," and "the" include plural referents unless the context clearly dictates otherwise.

The term "$C_{1-6}$-alkyl", alone or in combination with other groups, stands for a hydrocarbon radical which may be linear or branched, with single or multiple branching, wherein the alkyl group in general comprises 1 to 6 carbon atoms, for example, methyl (Me), ethyl (Et), propyl, isopropyl (i-propyl), n-butyl, i-butyl (isobutyl), 2-butyl (sec-butyl), t-butyl (tert-butyl), isopentyl, 2-ethyl-propyl (2-methyl-propyl), 1,2-dimethyl-propyl and the like. Specific groups are methyl and ethyl.

The term "halogen-$C_{1-6}$-alkyl", alone or in combination with other groups, refers to $C_{1-6}$-alkyl as defined herein, which is substituted by one or multiple halogen, particularly 1-5 halogen, more particularly 1-3 halogen. Particular halogen is fluoro. Particular "halogen-$C_{1-6}$-alkyl" is fluoro-$C_{1-6}$-alkyl and a particular "halogen-$C_{1-3}$-alkyl" is fluoro-$C_{1-3}$-alkyl. Examples are trifluoromethyl, difluoromethyl, fluoromethyl and the like.

The term "cyano", alone or in combination with other groups, refers to N≡C—(NC—).

The term "amino", alone or in combination with other groups, refers to NH2.

The term "hydroxy", alone or in combination with other groups, refers to OH.

The term "halogen", alone or in combination with other groups, denotes chloro (Cl), iodo (I), fluoro (F) and bromo (Br). A specific group is F.

The term "heteroaryl", alone or in combination with other groups, refers to an aromatic carbocyclic group of having a single 4 to 8 membered ring, in particular 5 to 8, or multiple condensed rings comprising 6 to 14, in particular 6 to 10 ring atoms and containing 1, 2 or 3 heteroatoms individually selected from N, O and S, in particular 1N or 2N, in which group at least one heterocyclic ring is aromatic. The term "5-membered heteroaryl" refers to a single 5-membered aromatic ring, containing 1 or 2 heteroatoms selected from N, O and S, in particular one N and one S, for example thiazolyl. A specific group is thiazol-2-yl. The term "6-membered heteroaryl" refers to a single 6-membered aromatic ring, containing 1 or 2 heteroatoms selected from N, O and S, in particular one N, for example pyridinyl. A specific group is 2-pyridyl. Examples of "heteroaryl" include benzofuryl, benzoimidazolyl, 1H-benzoimidazolyl, benzoxazinyl, benzoxazolyl, benzothiazinyl, benzothiazolyl, benzothienyl, benzotriazolyl, furyl, imidazolyl, indazolyl, 1H-indazolyl, indolyl, isoquinolinyl, isothiazolyl, isoxazolyl, oxazolyl, pyrazinyl, pyrazolyl (pyrazyl), 1H-pyrazolyl, pyrazolo[1,5-a]pyridinyl, pyridazinyl, pyridinyl, pyrimidinyl, pyrrolyl, quinolinyl, tetrazolyl, thiazolyl, thienyl, triazolyl, 6,7-dihydro-5H-[1]pyrindinyl and the like. Specific groups are pyridinyl and thiazolyl.

The term "$C_{1-6}$-alkoxy", alone or in combination with other groups, stands for an —O—$C_{1-6}$-alkyl radical which may be linear or branched, with single or multiple branching, wherein the alkyl group in general comprises 1 to 6 carbon atoms, for example, methoxy (OMe, MeO), ethoxy (OEt), propoxy, isopropoxy (i-propoxy), n-butoxy, i-butoxy (iso-butoxy), 2-butoxy (sec-butoxy), t-butoxy (tert-butoxy), isopentyloxy (i-pentyloxy) and the like. Particular "$C_{1-6}$-alkoxy" are groups with 1 to 4 carbon atoms. A specific group is methoxy.

The term "halogen-$C_{1-6}$-alkoxy", alone or in combination with other groups, refers to $C_{1-6}$-alkoxy as defined herein, which is substituted by one or multiple halogen, particularly 1-5 halogen, more particularly 1-3 halogen. Particular halogen is fluoro. Particular "halogen-$C_{1-6}$-alkoxy" is fluoro-$C_{1-6}$-alkoxy and a particular "halogen-$C_{1-3}$-alkoxy" is fluoro-$C_{1-3}$-alkoxy. A specific group is —O—$CF_3$.

The term "N-containing heterocyclyl" or "heterocyclyl" refers to a monovalent saturated or partly unsaturated mono- or bicyclic ring system of 4 to 9 ring atoms, comprising 1, 2, or 3 ring heteroatoms that are N, the remaining ring atoms being carbon. Bicyclic means consisting of two cycles having two ring atoms in common, i.e. the bridge separating the two rings is either a single bond or a chain of one or two ring atoms. Examples are piperidinyl and piperazinyl.

The term "aryl" denotes a monovalent aromatic carbocyclic mono- or bicyclic ring system comprising 6 to 10 carbon ring atoms. Examples of aryl moieties include phenyl and naphthyl. Specific "aryl" is phenyl.

The term "pharmaceutically acceptable" denotes an attribute of a material which is useful in preparing a pharmaceutical composition that is generally safe, non-toxic, and neither biologically nor otherwise undesirable and is acceptable for veterinary as well as human pharmaceutical use.

The term "a pharmaceutically acceptable salt" refers to a salt that is suitable for use in contact with the tissues of humans and animals. Examples of suitable salts with inorganic and organic acids are, but are not limited to acetic acid, citric acid, formic acid, fumaric acid, hydrochloric acid, lactic acid, maleic acid, malic acid, methane-sulfonic acid, nitric acid, phosphoric acid, p-toluenesulphonic acid, succinic acid, sulfuric acid (sulphuric acid), tartaric acid, trifluoroacetic acid and the like. Particular acids are formic acid, trifluoroacetic acid and hydrochloric acid. Specific acids are hydrochloric acid, trifluoroacetic acid and fumaric acid.

The terms "pharmaceutically acceptable auxiliary substance" refer to carriers and auxiliary substances such as diluents or excipients that are compatible with the other ingredients of the formulation.

The term "pharmaceutical composition" encompasses a product comprising specified ingredients in pre-determined amounts or proportions, as well as any product that results, directly or indirectly, from combining specified ingredients in specified amounts. Particularly it encompasses a product comprising one or more active ingredients, and an optional carrier comprising inert ingredients, as well as any product that results, directly or indirectly, from combination, complexation or aggregation of any two or more of the ingredients, or from dissociation of one or more of the ingredients, or from other types of reactions or interactions of one or more of the ingredients.

The term "inhibitor" denotes a compound which competes with, reduces or prevents the binding of a particular ligand to particular receptor or which reduces or prevents the function of a particular protein.

The term "half maximal inhibitory concentration" (IC$_{50}$) denotes the concentration of a particular compound required for obtaining 50% inhibition of a biological process in vitro. IC$_{50}$ values can be converted logarithmically to pIC$_{50}$ values (−log IC$_{50}$), in which higher values indicate exponentially greater potency. The IC$_{50}$ value is not an absolute value but depends on experimental conditions e.g. concentrations employed. The IC$_{50}$ value can be converted to an absolute inhibition constant (Ki) using the Cheng-Prusoff equation (Biochem. Pharmacol. (1973) 22:3099).

"Therapeutically effective amount" means an amount of a compound that, when administered to a subject for treating a disease state, is sufficient to effect such treatment for the disease state. The "therapeutically effective amount" will vary depending on the compound, disease state being treated, the severity or the disease treated, the age and relative health of the subject, the route and form of administration, the judgment of the attending medical or veterinary practitioner, and other factors.

The term "as defined herein" and "as described herein" when referring to a variable incorporates by reference the broad definition of the variable as well as particularly, more particularly and most particularly definitions, if any.

The terms "treating", "contacting" and "reacting" when referring to a chemical reaction means adding or mixing two or more reagents under appropriate conditions to produce the indicated and/or the desired product. It should be appreciated that the reaction which produces the indicated and/or the desired product may not necessarily result directly from the combination of two reagents which were initially added, i.e., there may be one or more intermediates which are produced in the mixture which ultimately leads to the formation of the indicated and/or the desired product.

The term "aromatic" denotes the conventional idea of aromaticity as defined in the literature, in particular in IUPAC—Compendium of Chemical Terminology, 2nd, A. D. McNaught & A. Wilkinson (Eds). Blackwell Scientific Publications, Oxford (1997).

The term "pharmaceutically acceptable excipient" denotes any ingredient having no therapeutic activity and being non-toxic such as disintegrators, binders, fillers, solvents, buffers, tonicity agents, stabilizers, antioxidants, surfactants or lubricants used in formulating pharmaceutical products.

Whenever a chiral carbon is present in a chemical structure, it is intended that all stereoisomers associated with that chiral carbon are encompassed by the structure as pure stereoisomers as well as mixtures thereof.

The invention also provides pharmaceutical compositions, methods of using, and methods of preparing the aforementioned compounds.

All separate embodiments may be combined.

One embodiment of the invention provides a compound of formula I,

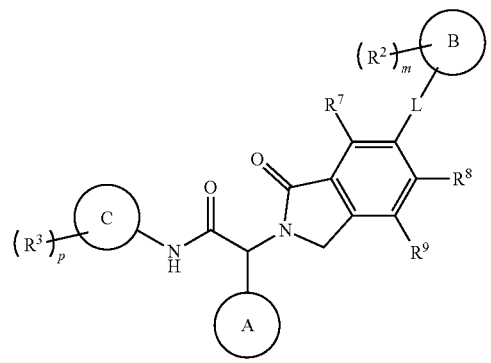

wherein
L is absent or —(C≡C)—,
A is

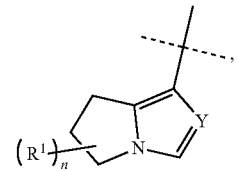

B is aryl or heteroaryl,
c is heteroaryl,
Y is N, C(OH) or CH,
R$^1$ is each independently selected from the group consisting of
  i) amino,
  ii) C$_{1-4}$-alkyl,
  iii) C$_{1-6}$-alkoxy,
  iv) cyano,
  v) halogen,
  vi) halogen-C$_{1-4}$-alkyl,
  vii) halogen-C$_{1-6}$-alkoxy, and
  viii) hydroxy;
R$^2$ is each independently selected from the group consisting of
  i) —(CH$_2$)$_k$—N(R$^4$, R$^5$),
  ii) —(C═O)—N(R$^4$, R$^5$),
  iii) halogen,
  iv) —NH—(C═O)—C$_{1-6}$-alkyl, and
  v) C$_{1-6}$-alkyl, optionally substituted by OH;
R$^3$ is each independently selected from the group consisting of
  i) amino,
  ii) C$_{1-6}$-alkyl,
  iii) C$_{1-6}$-alkoxy,
  iv) cyano,
  v) halogen,
  vi) halogen-C$_{1-6}$-alkyl,
  vii) halogen-C$_{1-6}$-alkoxy, and
  viii) hydroxy;
R$^4$ is each independently selected from the group consisting of
  i) H, and
  ii) C$_{1-6}$-alkyl;

$R^5$ is each independently selected from the group consisting of
  i) H,
  ii) $C_{1-6}$-alkyl, and
  iii) —(C=O)—$C_{1-6}$-alkyl;
or $R^4$ and $R^5$ form together with the N they are attached to a heterocyclyl, which heterocyclyl is optionally substituted by $R^6$.
$R^6$ is each independently selected from the group consisting of
  i) —OH,
  ii) $C_{1-6}$-alkyl, and
  iii) —(C=O)—$C_{1-6}$-alkyl;
$R^7$ is each independently selected from the group consisting of
  i) H,
  ii) halogen,
  iii) halogen-$C_{1-6}$-alkoxy,
  iv) $C_{1-6}$-alkoxy, and
  v) $C_{1-6}$-alkyl;
$R^8$ is each independently selected from the group consisting of
  i) H,
  ii) halogen,
  iii) $C_{1-6}$-alkoxy, and
  iv) $C_{1-6}$-alkyl;
$R^9$ is each independently selected from the group consisting of
  i) H,
  ii) halogen,
  iii) halogen-$C_{1-6}$-alkoxy,
  iv) $C_{1-6}$-alkoxy, and
  v) $C_{1-6}$-alkyl;
k is 0, 1 or 2,
n is 0, 1, 2, 3 or 4;
m is 0, 1 or 2;
P is 0 or 1;
or a pharmaceutically acceptable salt thereof.

A certain embodiment of the invention relates to the compound of formula I as described herein, or a pharmaceutically acceptable salt thereof, wherein
L is absent or —(C≡C)—,
A is

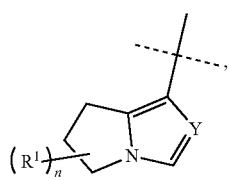

B is aryl or heteroaryl,
C is heteroaryl,
Y is N or CH,
$R^2$ is each independently selected from the group consisting of
  i) —(CH$_2$)$_k$—N($R^4$, $R^5$), and
  ii) $C_{1-6}$-alkyl, optionally substituted by OH;
$R^4$ and $R^5$ form together with the N they are attached to a heterocyclyl, which heterocyclyl is optionally substituted by $R^6$.
$R^6$ is each independently selected from the group consisting of
  i) —OH, and
  ii) $C_{1-6}$-alkyl;

$R^7$ is H or halogen;
$R^8$ is H;
$R^9$ is halogen;
k is 0 or 1;
n is 0;
m is 1;
p is 0.

A certain embodiment of the invention relates to the compound of formula I as described herein, or a pharmaceutically acceptable salt thereof, wherein A is

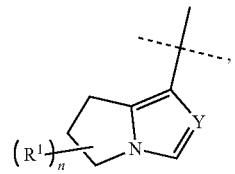

in particular

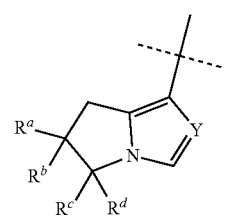

wherein
Y is N or CH, and
$R^a$, $R^b$, $R^c$ or $R^d$ is each independently selected from the group consisting of
  i) H,
  ii) amino,
  iii) $C_{1-6}$-alkyl,
  iv) $C_{1-6}$-alkoxy,
  v) cyano,
  vi) halogen,
  vii) halogen-$C_{1-6}$-alkyl,
  viii) halogen-$C_{1-6}$-alkoxy, and
  ix) hydroxyl;
more particularly, wherein A is 6,7-Dihydro-5H-pyrrolo[1,2-c]imidazol-1-yl or 6,7-Dihydro-5H-pyrrolizin-1-yl.

A certain embodiment of the invention relates to the compound of formula I as described herein, or a pharmaceutically acceptable salt thereof, wherein A is

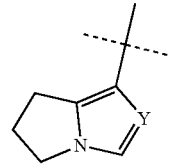

and Y is N or CH.

A certain embodiment of the invention relates to the compound of formula I as described herein, or a pharmaceutically acceptable salt thereof, wherein A is 6,7-Dihydro-5H-pyrrolo[1,2-c]imidazol-1-yl.

A certain embodiment of the invention relates to the compound of formula I as described herein, or a pharmaceutically acceptable salt thereof, wherein B is aryl, in particular phenyl.

A certain embodiment of the invention relates to the compound of formula I as described herein, or a pharmaceutically acceptable salt thereof, wherein B is aryl.

A certain embodiment of the invention relates to the compound of formula I as described herein, or a pharmaceutically acceptable salt thereof, wherein B is phenyl.

A certain embodiment of the invention relates to the compound of formula I as described herein, or a pharmaceutically acceptable salt thereof, wherein B is heteroaryl, in particular pyridinyl.

A certain embodiment of the invention relates to the compound of formula I as described herein, or a pharmaceutically acceptable salt thereof, wherein B is heteroaryl.

A certain embodiment of the invention relates to the compound of formula I as described herein, or a pharmaceutically acceptable salt thereof, wherein B is pyridinyl.

A certain embodiment of the invention relates to the compound of formula I as described herein, or a pharmaceutically acceptable salt thereof, wherein B is phenyl or pyridinyl.

A certain embodiment of the invention relates to the compound of formula I as described herein, or a pharmaceutically acceptable salt thereof, wherein C is heteroaryl, in particular thiazolyl.

A certain embodiment of the invention relates to the compound of formula I as described herein, or a pharmaceutically acceptable salt thereof, wherein C is heteroaryl.

A certain embodiment of the invention relates to the compound of formula I as described herein, or a pharmaceutically acceptable salt thereof, wherein C is thiazolyl.

A certain embodiment of the invention relates to the compound of formula I as described herein, or a pharmaceutically acceptable salt thereof, wherein n is 0, 1 or 2.

A certain embodiment of the invention relates to the compound of formula I as described herein, or a pharmaceutically acceptable salt thereof, wherein n is 0.

A certain embodiment of the invention relates to the compound of formula I as described herein, or a pharmaceutically acceptable salt thereof, wherein m is 1.

A certain embodiment of the invention relates to the compound of formula I as described herein, or a pharmaceutically acceptable salt thereof, wherein p is 0.

A certain embodiment of the invention relates to the compound of formula I as described herein, or a pharmaceutically acceptable salt thereof, wherein $R^2$ is —$(CH_2)_k$—$N(R^4, R^5)$, k is 0 or 1 and $R^4$ and $R^5$ form together with the N they are attached to a heterocyclyl, which heterocyclyl is optionally substituted by methyl, ethyl or OH, in particular wherein $R^2$ is (ethyl)piperazinyl, (hydroxy)piperidinyl, —$CH_2$-(hydroxy)-piperidinyl, —$CH_2$-(methyl)piperazinyl, or -piperazinyl.

A certain embodiment of the invention relates to the compound of formula I as described herein, or a pharmaceutically acceptable salt thereof, wherein $R^2$ is —$(CH_2)_k$—$N(R^4, R^5)$, k is 0 or 1 and $R^4$ and $R^5$ form together with the N they are attached to a heterocyclyl, which heterocyclyl is optionally substituted by methyl, ethyl or OH.

A certain embodiment of the invention relates to the compound of formula I as described herein, or a pharmaceutically acceptable salt thereof, wherein $R^2$ is —$(CH_2)_k$—$N(R^4, R^5)$, k is 0 and $R^4$ and $R^5$ form together with the N they are attached to a heterocyclyl, which heterocyclyl is optionally substituted by methyl, ethyl or OH.

A certain embodiment of the invention relates to the compound of formula I as described herein, or a pharmaceutically acceptable salt thereof, wherein $R^2$ is —$(CH_2)_k$—$N(R^4, R^5)$, k is 1 and $R^4$ and $R^5$ form together with the N they are attached to a heterocyclyl, which heterocyclyl is optionally substituted by methyl, ethyl or OH.

A certain embodiment of the invention relates to the compound of formula I as described herein, or a pharmaceutically acceptable salt thereof, wherein $R^2$ is (ethyl)piperazinyl, (hydroxy)piperidinyl, —$CH_2$-(hydroxy)-piperidinyl, —$CH_2$-(methyl)piperazinyl, or -piperazinyl.

A certain embodiment of the invention relates to the compound of formula I as described herein, or a pharmaceutically acceptable salt thereof, wherein $R^9$ is halogen.

A certain embodiment of the invention relates to the compound of formula I as described herein, or a pharmaceutically acceptable salt thereof, wherein $R^9$ is F.

A certain embodiment of the invention relates to the compound of formula I as described herein, or a pharmaceutically acceptable salt thereof, that is selected from the group consisting of (2RS)-2-(6,7-Dihydro-5H-pyrrolizin-1-yl)-2-[4-fluoro-6-[2-[4-[(4-hydroxy-1-piperidyl)methyl]phenyl]ethynyl]-1-oxo-isoindolin-2-yl]-N-thiazol-2-yl-acetamide, (2RS)-2-(6,7-Dihydro-5H-pyrrolo[1,2-c]imidazol-1-yl)-2-[4-fluoro-6-[2-[4-[(4-methylpiperazin-1-yl)methyl]phenyl]ethynyl]-1-oxo-isoindolin-2-yl]-N-thiazol-2-yl-acetamide, (2RS)-2-(6,7-Dihydro-5H-pyrrolo[1,2-c]imidazol-1-yl)-2-[4-fluoro-6-[2-[4-[(4-hydroxy-1-piperidyl)methyl]phenyl]ethynyl]-1-oxo-isoindolin-2-yl]-N-thiazol-2-yl-acetamide, (2RS)-2-(6,7-Dihydro-5H-pyrrolo[1,2-c]imidazol-1-yl)-2-[4-fluoro-1-oxo-6-(4-piperazin-1-ylphenyl)isoindolin-2-yl]-N-thiazol-2-yl-acetamide, (2RS)-2-(6,7-Dihydro-5H-pyrrolo[1,2-c]imidazol-1-yl)-2-[4-fluoro-6-[4-(4-hydroxy-1-piperidyl)phenyl]-1-oxo-isoindolin-2-yl]-N-thiazol-2-yl-acetamide, (2RS)-2-(6,7-Dihydro-5H-pyrrolo[1,2-c]imidazol-1-yl)-2-[4-fluoro-6-[2-[4-(hydroxymethyl)phenyl]ethynyl]-1-oxo-isoindolin-2-yl]-N-thiazol-2-yl-acetamide, (2RS)-2-(6,7-Dihydro-5H-pyrrolo[1,2-c]imidazol-1-yl)-2-[4-fluoro-1-oxo-6-[2-[4-(1-piperidylmethyl)phenyl]ethynyl]isoindolin-2-yl]-N-thiazol-2-yl-acetamide, (2RS)-2-(6,7-Dihydro-5H-pyrrolo[1,2-c]imidazol-1-yl)-2-[6-[4-(4-ethylpiperazin-1-yl)phenyl]-4-fluoro-1-oxo-isoindolin-2-yl]-N-thiazol-2-yl-acetamide, (2RS)-2-(6,7-Dihydro-5H-pyrrolo[1,2-c]imidazol-1-yl)-2-[6-[6-(4-ethylpiperazin-1-yl)-3-pyridyl]-4-fluoro-1-oxo-isoindolin-2-yl]-N-thiazol-2-yl-acetamide, (2RS)-2-[4-Chloro-6-[2-[4-[(4-hydroxy-1-piperidyl)methyl]phenyl]ethynyl]-1-oxo-isoindolin-2-yl]-2-(6,7-dihydro-5H-pyrrolo[1,2-c]imidazol-1-yl)-N-thiazol-2-yl-acetamide, (2RS)-2-[4-Chloro-6-[4-(4-ethylpiperazin-1-yl)phenyl]-1-oxo-isoindolin-2-yl]-2-(6,7-dihydro-5H-pyrrolo[1,2-c]imidazol-1-yl)-N-thiazol-2-yl-acetamide, (2RS)-2-[4-Chloro-6-[4-(4-hydroxy-1-piperidyl)phenyl]-1-oxo-isoindolin-2-yl]-2-(6,7-dihydro-5H-pyrrolo[1,2-c]imidazol-1-yl)-N-thiazol-2-yl-acetamide, (2RS)-2-[4-Chloro-6-[6-(4-hydroxy-1-piperidyl)-3-pyridyl]-1-oxo-isoindolin-2-yl]-2-(6,7-dihydro-5H-pyrrolo[1,2-c]imidazol-1-yl)-N-thiazol-2-yl-acetamide, and (2RS)-2-[7-chloro-4-fluoro-6-[2-[4-[(4-hydroxy-1-piperidyl)methyl]phenyl]ethynyl]-1-oxo-isoindolin-2-yl]-2-(6,7-dihydro-5H-pyrrolo[1,2-c]imidazol-1-yl)-N-thiazol-2-yl-acetamide.

A certain embodiment of the invention relates to the compound of formula I as described herein, or a pharmaceutically acceptable salt thereof, that is selected from the group consisting of (2RS)-2-(6,7-Dihydro-5H-pyrrolizin-1-yl)-2-[4-fluoro-6-[2-[4-[(4-hydroxy-1-piperidyl)methyl]phenyl]ethynyl]-1-oxo-isoindolin-2-yl]-N-thiazol-2-yl-acetamide, (2RS)-2-(6,7-Dihydro-5H-pyrrolo[1,2-c]imidazol-1-yl)-2-[4-fluoro-6-[2-[4-[(4-methylpiperazin-1-yl)methyl]phenyl]ethynyl]-1-oxo-isoindolin-2-yl]-N-thiazol-2-yl-acetamide, (2RS)-2-(6,7-Dihydro-5H-pyrrolo[1,2-c]imidazol-1-yl)-2-[4-fluoro-6-[2-[4-[(4-hydroxy-1-piperidyl)methyl]phenyl]ethynyl]-1-oxo-isoindolin-2-yl]-N-thiazol-2-yl-acetamide, (2RS)-2-(6,7-Dihydro-5H-pyrrolo[1,2-c]imidazol-1-yl)-2-[4-fluoro-1-oxo-6-(4-piperazin-1-ylphenyl)isoindolin-2-yl]-N-thiazol-2-yl-acetamide, (2RS)-2-(6,7-Dihydro-5H-pyrrolo[1,2-c]imidazol-1-yl)-2-[4-fluoro-6-[4-(4-hydroxy-1-piperidyl)phenyl]-1-oxo-isoindolin-2-yl]-N-thiazol-2-yl-acetamide, (2RS)-2-(6,7-Dihydro-5H-pyrrolo[1,2-c]imidazol-1-yl)-2-[4-fluoro-1-oxo-6-[2-[4-(1-piperidylmethyl)phenyl]ethynyl]isoindolin-2-yl]-N-thiazol-2-yl-acetamide, (2RS)-2-(6,7-Dihydro-5H-pyrrolo[1,2-c]imidazol-1-yl)-2-[6-[4-(4-ethylpiperazin-1-yl)phenyl]-4-fluoro-1-oxo-isoindolin-2-yl]-N-thiazol-2-yl-acetamide, (2RS)-2-(6,7-Dihydro-5H-pyrrolo[1,2-c]imidazol-1-yl)-2-[6-[6-(4-ethylpiperazin-1-yl)-3-pyridyl]-4-fluoro-1-oxo-isoindolin-2-yl]-N-thiazol-2-yl-acetamide, (2RS)-2-[4-Chloro-6-[2-[4-[(4-hydroxy-1-piperidyl)methyl]phenyl]ethynyl]-1-oxo-isoindolin-2-yl]-2-(6,7-dihydro-5H-pyrrolo[1,2-c]imidazol-1-yl)-N-thiazol-2-yl-acetamide, (2RS)-2-[4-Chloro-6-[4-(4-ethylpiperazin-1-yl)phenyl]-1-oxo-isoindolin-2-yl]-2-(6,7-dihydro-5H-pyrrolo[1,2-c]imidazol-1-yl)-N-thiazol-2-yl-acetamide, (2RS)-2-[4-Chloro-6-[4-(4-hydroxy-1-piperidyl)phenyl]-1-oxo-isoindolin-2-yl]-2-(6,7-dihydro-5H-pyrrolo[1,2-c]imidazol-1-yl)-N-thiazol-2-yl-acetamide, (2RS)-2-[4-Chloro-6-[6-(4-hydroxy-1-piperidyl)-3-pyridyl]-1-oxo-isoindolin-2-yl]-2-(6,7-dihydro-5H-pyrrolo[1,2-c]imidazol-1-yl)-N-thiazol-2-yl-acetamide, and (2RS)-2-[7-chloro-4-fluoro-6-[2-[4-[(4-hydroxy-1-piperidyl)methyl]phenyl]ethynyl]-1-oxo-isoindolin-2-yl]-2-(6,7-dihydro-5H-pyrrolo[1,2-c]imidazol-1-yl)-N-thiazol-2-yl-acetamide.

A certain embodiment of the invention relates to the compound of formula I as described herein, or a pharmaceutically acceptable salt thereof, for use as therapeutically active substance.

A certain embodiment of the invention relates to the compound of formula I as described herein, or a pharmaceutically acceptable salt thereof, for the use in the therapeutic and/or prophylactic treatment of cancer, in particular non-small-cell lung cancer.

A certain embodiment of the invention relates to the compound of formula I as described herein, or a pharmaceutically acceptable salt thereof, for the use in the therapeutic and/or prophylactic treatment of non-small-cell lung cancer.

A certain embodiment of the invention relates to the compound of formula I as described herein, or a pharmaceutically acceptable salt thereof, for the manufacture of a medicament for the therapeutic and/or prophylactic treatment of cancer, in particular non-small-cell lung cancer.

A certain embodiment of the invention relates to a pharmaceutical composition comprising the compound of formula I as described herein, or a pharmaceutically acceptable salt thereof, and a pharmaceutically acceptable auxiliary substance.

A certain embodiment of the invention relates to a method for the therapeutic and/or prophylactic treatment of cancer, in particular non-small-cell lung cancer by administering the compound of formula I as described herein, or a pharmaceutically acceptable salt thereof, to a patient.

A certain embodiment of the invention relates to the compound of formula I as described herein, or a pharmaceutically acceptable salt thereof, for the use as a medicament in therapeutic and/or prophylactic treatment of a patient with EGFR activating mutations suffering from cancer, in particular non-small-cell lung cancer, comprising determining the EGFR activating mutations status in said patient and then administering the compound of formula I as described herein, or a pharmaceutically acceptable salt thereof, to said patient.

A certain embodiment of the invention relates to the compound of formula I as described herein, or a pharmaceutically acceptable salt thereof, for the use as a medicament in therapeutic and/or prophylactic treatment of a patient with EGFR mutations T790M/L858R, T790M/L858R/C797S, L858R and/or L858R/C797S suffering from cancer, in particular non-small-cell lung cancer, comprising determining the EGFR activating mutations status in said patient and then administering the compound of formula I as described herein, or a pharmaceutically acceptable salt thereof, to said patient.

A certain embodiment of the invention relates to the compound of formula I as described herein, or a pharmaceutically acceptable salt thereof, for the use as a medicament in therapeutic and/or prophylactic treatment of a patient with EGFR activating mutations as determined with a Cobas® EGFR Mutation Test v2 suffering from cancer, in particular non-small-cell lung cancer, comprising determining the EGFR activating mutations status in said patient and then administering the compound of formula I as described herein, or a pharmaceutically acceptable salt thereof, to said patient.

Furthermore, the invention includes all substituents in its corresponding deuterated form, wherever applicable, of the compounds of formula I.

Furthermore, the invention includes all optical isomers, i.e. diastereoisomers, diastereomeric mixtures, racemic mixtures, all their corresponding enantiomers and/or tautomers as well as their solvates, wherever applicable, of the compounds of formula I.

The compounds of formula I may contain one or more asymmetric centers and can therefore occur as racemates, racemic mixtures, single enantiomers, diastereomeric mixtures and individual diastereomers. Additional asymmetric centers may be present depending upon the nature of the various substituents on the molecule. Each such asymmetric center will independently produce two optical isomers and it is intended that all of the possible optical isomers and diastereomers in mixtures and as pure or partially purified compounds are included within this invention. The present invention is meant to encompass all such isomeric forms of these compounds. The independent syntheses of these diastereomers or their chromatographic separations may be achieved as known in the art by appropriate modification of the methodology disclosed herein. Their absolute stereochemistry may be determined by the x-ray crystallography of crystalline products or crystalline intermediates which are derivatized, if necessary, with a reagent containing an asymmetric center of known absolute configuration. If desired, racemic mixtures of the compounds may be separated so that the individual enantiomers are isolated. The separation can be carried out by methods well known in the art, such as the coupling of a racemic mixture of compounds to an enantiomerically pure compound to form a diastereomeric mixture, followed by separation of the individual diastereomers by standard methods, such as fractional crystallization or chromatography.

In the embodiments, where optically pure enantiomers are provided, optically pure enantiomer means that the compound contains >90% of the desired isomer by weight, particularly >95% of the desired isomer by weight, or more particularly >99% of the desired isomer by weight, said weight percent based upon the total weight of the isomer(s) of the compound. Chirally pure or chirally enriched compounds may be prepared by chirally selective synthesis or by separation of enantiomers. The separation of enantiomers may be carried out on the final product or alternatively on a suitable intermediate.

The compounds of formula I may be prepared in accordance with the schemes described in the examples. The starting material is commercially available or may be prepared in accordance with known methods.

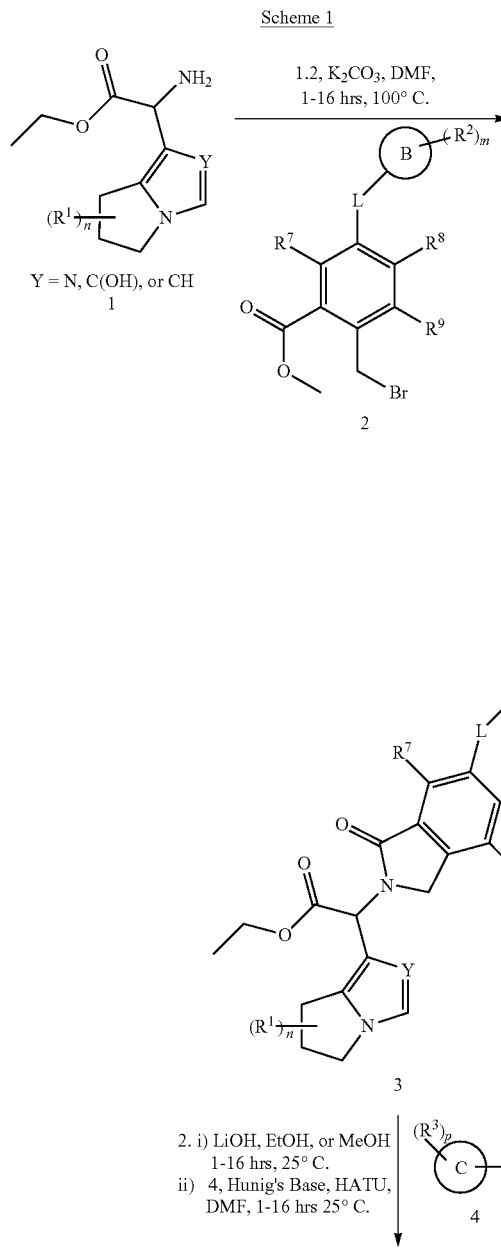

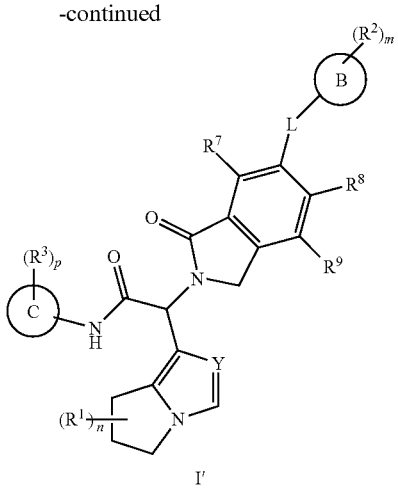

An isoindoline based compound of general formula I' can be obtained for example by ring cyclization of a previously prepared aminoester 1 with an appropriately substituted methyl 2-(bromomethyl)benzoate of formula 2 to yield the desired isoindoline ester 3. Saponification and amide coupling with an appropriately substituted amine of formula 4 with a coupling agent such as HATU yields the desired isoindoline compound of general formula I' (scheme 1).

Generally speaking, the sequence of steps used to synthesize the compounds of formula I', which is a compound of formula I, and further functionalization can also be modified in certain cases.

The corresponding pharmaceutically acceptable salts with acids can be obtained by standard methods known to the person skilled in the art, e.g. by dissolving the compound of formula I in a suitable solvent such as e.g. dioxane or tetrahydrofuran and adding an appropriate amount of the corresponding acid. The products can usually be isolated by filtration or by chromatography. The conversion of a compound of formula I into a pharmaceutically acceptable salt with a base can be carried out by treatment of such a compound with such a base. One possible method to form such a salt is e.g. by addition of 1/n equivalents of a basic salt such as e.g. $M(OH)_n$, wherein M=metal or ammonium cation and n=number of hydroxide anions, to a solution of the compound in a suitable solvent (e.g. ethanol, ethanol-water mixture, tetrahydrofuran-water mixture) and to remove the solvent by evaporation or lyophilisation. Particular salts are hydrochloride, formate and trifluoroacetate.

Insofar as their preparation is not described in the examples, the compounds of formula I as well as all intermediate products can be prepared according to analogous methods or according to the methods set forth herein. Starting materials are commercially available, known in the art or can be prepared by methods known in the art or in analogy thereto.

It will be appreciated that the compounds of general formula I in this invention may be derivatised at functional groups to provide derivatives which are capable of conversion back to the parent compound in vivo.

Pharmacological Tests

The compounds of formula I and their pharmaceutically acceptable salts possess valuable pharmacological properties. The compounds were investigated in accordance with the test given hereinafter.

HTRF Phospho EGFR TMLR Assay (Cellular)

Cell Line and Media

H1975 cell line (CRL-5908; Lot BA70803) was obtained from American Type Culture Collection (Manassas, VA, USA). Cells were maintained at 37° C., 5% $CO_2$ in complete Media RPMI 1640 without phenol red containing 0.3 mg/ml glutamine, 100 IU/ml penicillin, and 100 mg/ml streptomycin (Gibco, 15140-122) supplemented with 10% fetal bovine serum (FBS, Gibco, 10091-148). Compounds were diluted into starving medium RPMI 1640 Media (Gibco, 11835-030) without phenol red containing 0.3 mg/ml glutamine, 100 IU/ml penicillin, and 100 mg/ml streptomycin (Gibco).

Protocol

Cells were cultured for 24 h in a 384-well plate (Greiner Bio-One, Nr. 784-080; 5000 cells/well) using 8 μl of complete medium/well. Then 4 μl/well of the 3× compound solution, containing a factor 3 dilution series of the compound or DMSO in starving medium, were added to the cells (final DMSO 0.33%). After 16 hours at 37° C., 5% CO2, 95% rel. humidity cells were lysed by adding to the compound mix 4 μl/well of the supplemented lysis buffer (Cisbio, Phospho-EGFR HTRF kit, 64EG1PEH), followed by incubation for 30 min at room temperature with shaking (400 rpm). Then 4 μl of a mixture of anti-Phospho-EGFR Cryptate and of anti-Phospho-EGFR-d2 antibody solutions prepared in the detection buffer was added. The plates were then incubated for 4 h at room temperature before reading the fluorescence emission at 620 and 665 nm using an Envision reader (Perkin Elmer).

TABLE 1

H1975 cellular HTRF Phospho EGFR TMLR assay data

| Exam. | Structure | $IC_{50}$ (H1975) |
|---|---|---|
| 1 | 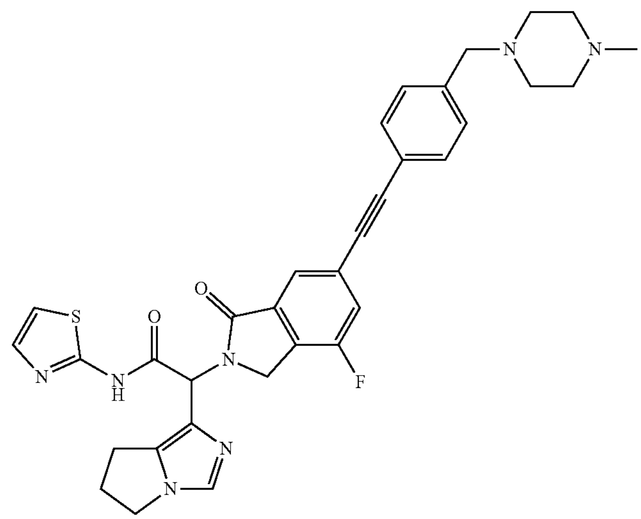 [SMILES: CN1CCN(Cc2ccc(C#Cc3cc(F)c4c(c3)C(=O)N(C(C(=O)Nc3nccs3)c3ncn5c3CCC5)C4)cc2)CC1] | 3 nM |
| 2 | 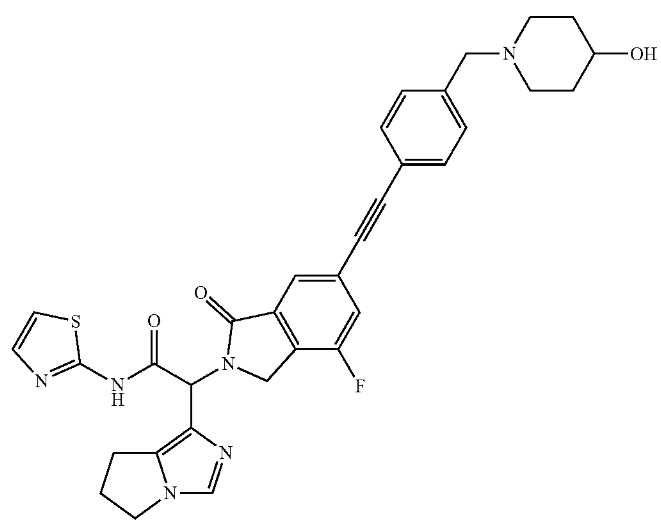 | 1 nM |

TABLE 1-continued

H1975 cellular HTRF Phospho EGFR TMLR assay data

| Exam. | Structure | IC$_{50}$ (H1975) |
|---|---|---|
| 3 | 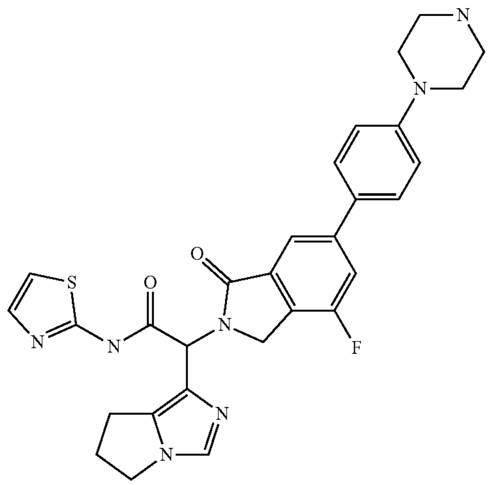 [SMILES: O=C(Nc1nccs1)C(c1ncn2c1CCC2)N1Cc2c(F)cc(-c3ccc(N4CCNCC4)cc3)cc2C1=O] | 2 nM |
| 4 | 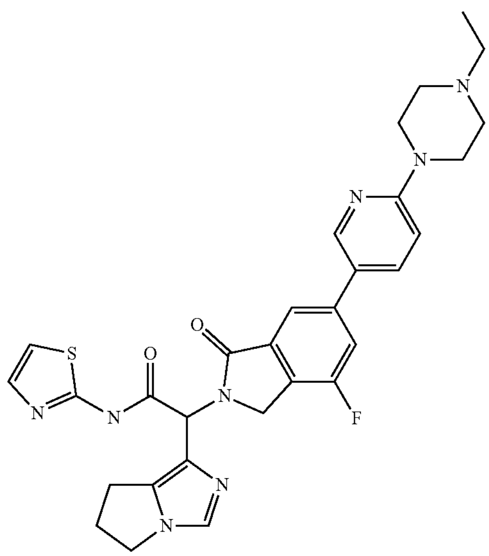 [SMILES: CCN1CCN(c2ccc(-c3cc(F)c4c(c3)C(=O)N(C(C(=O)Nc3nccs3)c3ncn5c3CCC5)C4)cn2)CC1] | 4 nM |
| 5 | 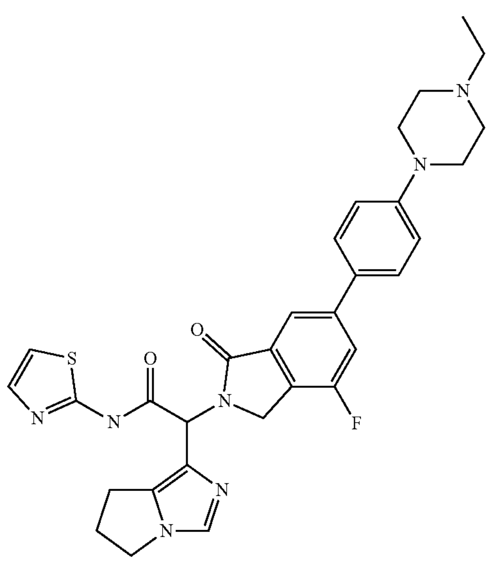 [SMILES: CCN1CCN(c2ccc(-c3cc(F)c4c(c3)C(=O)N(C(C(=O)Nc3nccs3)c3ncn5c3CCC5)C4)cc2)CC1] | 3 nM |

TABLE 1-continued
H1975 cellular HTRF Phospho EGFR TMLR assay data
| Exam. | Structure | IC$_{50}$ (H1975) |
|---|---|---|
| 6 | 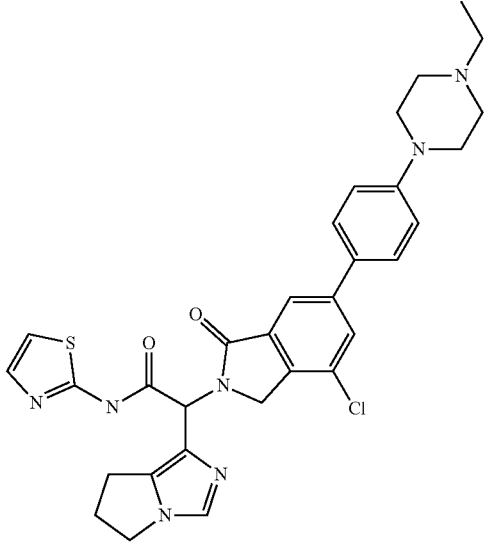 [SMILES: CCN1CCN(c2ccc(-c3cc(Cl)c4c(c3)C(=O)N(C(C(=O)Nc3nccs3)c3ncn5c3CCC5)C4)cc2)CC1] | 4 nM |
| 7 | 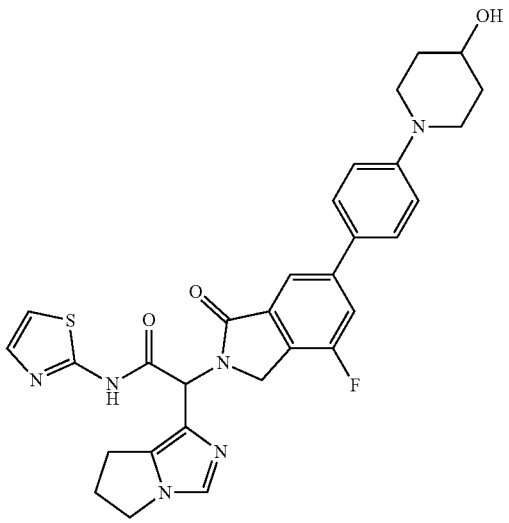 [SMILES: O=C(Nc1nccs1)C(c1ncn2c1CCC2)N1Cc2c(F)cc(-c3ccc(N4CCC(O)CC4)cc3)cc2C1=O] | 1 nM |

TABLE 1-continued
H1975 cellular HTRF Phospho EGFR TMLR assay data
| Exam. | Structure | IC$_{50}$ (H1975) |
|---|---|---|
| 8 | 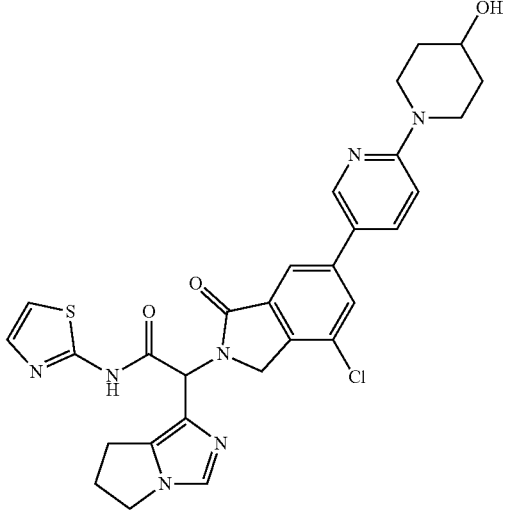 [SMILES: O=C(Nc1nccs1)C(c1ncn2c1CCC2)N1Cc2c(Cl)cc(-c3ccc(N4CCC(O)CC4)nc3)cc2C1=O] | 2 nM |
| 9 | 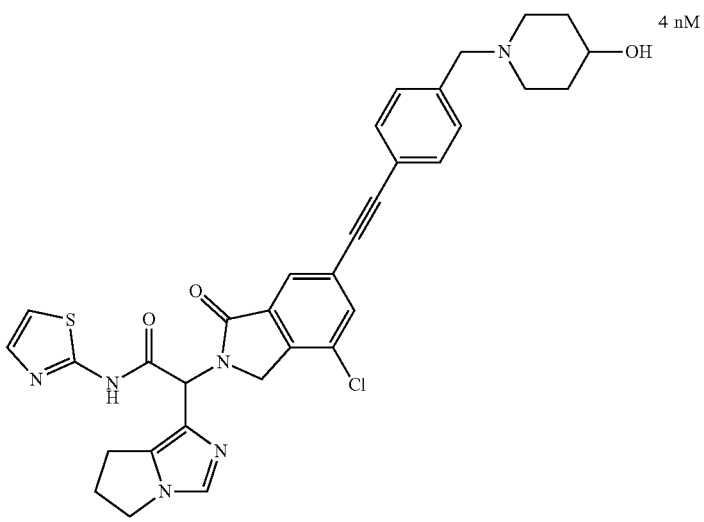 | 4 nM |
| 10 | 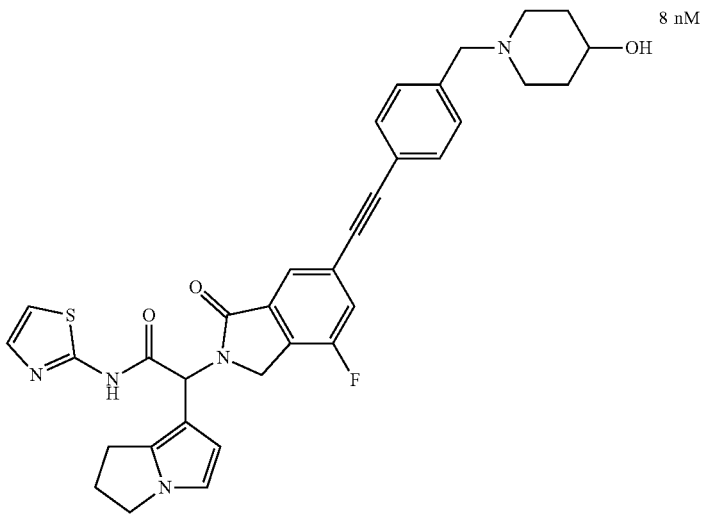 | 8 nM |

TABLE 1-continued
H1975 cellular HTRF Phospho EGFR TMLR assay data
| Exam. | Structure | IC$_{50}$ (H1975) |
|---|---|---|
| 11 | 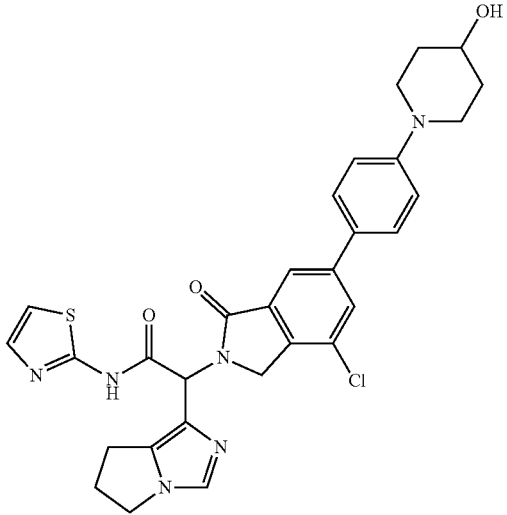 [SMILES: O=C(Nc1nccs1)C(c1ncn2c1CCC2)N1Cc2c(Cl)cc(-c3ccc(N4CCC(O)CC4)cc3)cc2C1=O] | 2 nM |
| 12 | 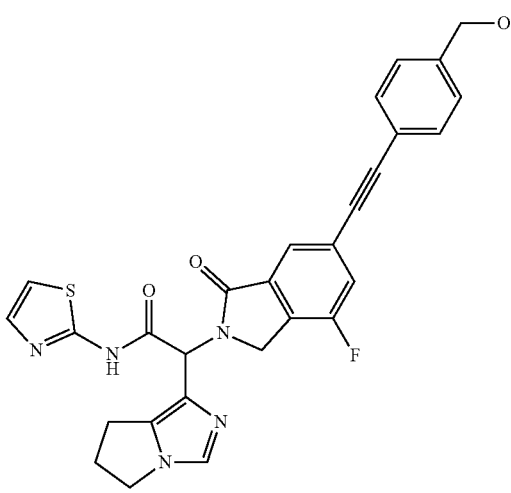 | 2 nM |
| 13 | 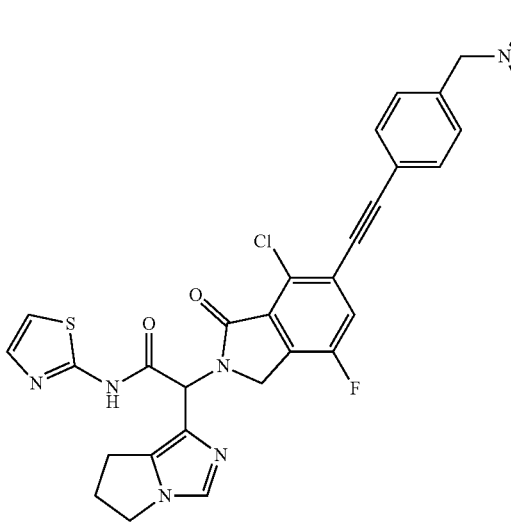 | 3 nM |

TABLE 1-continued

H1975 cellular HTRF Phospho EGFR TMLR assay data

| Exam. | Structure | IC$_{50}$ (H1975) |
|---|---|---|
| 14 | 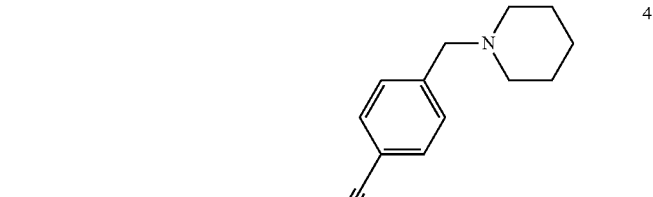 | 4 nM |

Pharmaceutical Compositions

The compounds of formula I and the pharmaceutically acceptable salts can be used as therapeutically active substances, e.g. in the form of pharmaceutical preparations. The pharmaceutical preparations can be administered orally, e.g. in the form of tablets, coated tablets, dragées, hard and soft gelatin capsules, solutions, emulsions or suspensions. The administration can, however, also be effected rectally, e.g. in the form of suppositories, or parenterally, e.g. in the form of injection solutions.

The compounds of formula I and the pharmaceutically acceptable salts thereof can be processed with pharmaceutically inert, inorganic or organic carriers for the production of pharmaceutical preparations. Lactose, corn starch or derivatives thereof, talc, stearic acids or its salts and the like can be used, for example, as such carriers for tablets, coated tablets, dragées and hard gelatin capsules. Suitable carriers for soft gelatin capsules are, for example, vegetable oils, waxes, fats, semi-solid and liquid polyols and the like. Depending on the nature of the active substance no carriers are however usually required in the case of soft gelatin capsules. Suitable carriers for the production of solutions and syrups are, for example, water, polyols, glycerol, vegetable oil and the like. Suitable carriers for suppositories are, for example, natural or hardened oils, waxes, fats, semi-liquid or liquid polyols and the like.

The pharmaceutical preparations can, moreover, contain pharmaceutically acceptable auxiliary substances such as preservatives, solubilizers, stabilizers, wetting agents, emulsifiers, sweeteners, colorants, flavorants, salts for varying the osmotic pressure, buffers, masking agents or antioxidants. They can also contain still other therapeutically valuable substances.

Medicaments containing a compound of formula I or a pharmaceutically acceptable salt thereof and a therapeutically inert carrier are also provided by the present invention, as is a process for their production, which comprises bringing one or more compounds of formula I and/or pharmaceutically acceptable salts thereof and, if desired, one or more other therapeutically valuable substances into a galenical administration form together with one or more therapeutically inert carriers.

The dosage can vary within wide limits and will, of course, have to be adjusted to the individual requirements in each particular case. In the case of oral administration the dosage for adults can vary from about 0.01 mg to about 1000 mg per day of a compound of general formula I or of the corresponding amount of a pharmaceutically acceptable salt thereof. The daily dosage may be administered as single dose or in divided doses and, in addition, the upper limit can also be exceeded when this is found to be indicated.

The following examples illustrate the present invention without limiting it, but serve merely as representative thereof. The pharmaceutical preparations conveniently contain about 1-500 mg, particularly 1-100 mg, of a compound of formula I. Examples of compositions according to the invention are:

Example A

Tablets of the following composition are manufactured in the usual manner:

TABLE 2 possible tablet composition

| | mg/tablet | | | |
|---|---|---|---|---|
| ingredient | 5 | 25 | 100 | 500 |
| Compound of formula I | 5 | 25 | 100 | 500 |
| Lactose Anhydrous DTG | 125 | 105 | 30 | 150 |
| Sta-Rx 1500 | 6 | 6 | 6 | 60 |
| Microcrystalline Cellulose | 30 | 30 | 30 | 450 |
| Magnesium Stearate | 1 | 1 | 1 | 1 |
| Total | 167 | 167 | 167 | 831 |

Manufacturing Procedure
1. Mix ingredients 1, 2, 3 and 4 and granulate with purified water.
2. Dry the granules at 50° ° C.
3. Pass the granules through suitable milling equipment.
4. Add ingredient 5 and mix for three minutes; compress on a suitable press.

Example B-1

Capsules of the following composition are manufactured:

TABLE 3 possible capsule ingredient composition

| ingredient | mg/capsule | | | |
|---|---|---|---|---|
| | 5 | 25 | 100 | 500 |
| Compound of formula I | 5 | 25 | 100 | 500 |
| Hydrous Lactose | 159 | 123 | 148 | — |
| Corn Starch | 25 | 35 | 40 | 70 |
| Talc | 10 | 15 | 10 | 25 |
| Magnesium Stearate | 1 | 2 | 2 | 5 |
| Total | 200 | 200 | 300 | 600 |

Manufacturing Procedure
1. Mix ingredients 1, 2 and 3 in a suitable mixer for 30 minutes.
2. Add ingredients 4 and 5 and mix for 3 minutes.
3. Fill into a suitable capsule.

The compound of formula I, lactose and corn starch are firstly mixed in a mixer and then in a comminuting machine. The mixture is returned to the mixer; the talc is added thereto and mixed thoroughly. The mixture is filled by machine into suitable capsules, e.g. hard gelatin capsules.

Example B-2

Soft Gelatin Capsules of the following composition are manufactured:

TABLE 4 possible soft gelatin capsule ingredient composition

| ingredient | mg/capsule |
|---|---|
| Compound of formula I | 5 |
| Yellow wax | 8 |
| Hydrogenated Soya bean oil | 8 |
| Partially hydrogenated plant oils | 34 |
| Soya bean oil | 110 |
| Total | 165 |

TABLE 5 possible soft gelatin capsule composition

| ingredient | mg/capsule |
|---|---|
| Gelatin | 75 |
| Glycerol 85% | 32 |
| Karion 83 | 8 (dry matter) |
| Titan dioxide | 0.4 |
| Iron oxide yellow | 1.1 |
| Total | 116.5 |

Manufacturing Procedure

The compound of formula I is dissolved in a warm melting of the other ingredients and the mixture is filled into soft gelatin capsules of appropriate size. The filled soft gelatin capsules are treated according to the usual procedures.

Example C

Suppositories of the following composition are manufactured:

TABLE 6 possible suppository composition

| ingredient | mg/supp. |
|---|---|
| Compound of formula I | 15 |
| Suppository mass | 1285 |
| Total | 1300 |

Manufacturing Procedure

The suppository mass is melted in a glass or steel vessel, mixed thoroughly and cooled to 45° C. Thereupon, the finely powdered compound of formula I is added thereto and stirred until it has dispersed completely. The mixture is poured into suppository moulds of suitable size, left to cool; the suppositories are then removed from the moulds and packed individually in wax paper or metal foil.

Example D

Injection solutions of the following composition are manufactured:

TABLE 7 possible injection solution composition

| ingredient | mg/injection solution. |
|---|---|
| Compound of formula I | 3 |
| Polyethylene Glycol 400 | 150 |
| acetic acid | q.s. ad pH 5.0 |
| water for injection solutions | ad 1.0 ml |

Manufacturing Procedure

The compound of formula I is dissolved in a mixture of Polyethylene Glycol 400 and water for injection (part). The pH is adjusted to 5.0 by acetic acid. The volume is adjusted to 1.0 ml by addition of the residual amount of water. The solution is filtered, filled into vials using an appropriate overage and sterilized.

Example E

Sachets of the following composition are manufactured:

TABLE 8 possible sachet composition

| ingredient | mg/sachet |
|---|---|
| Compound of formula I | 50 |
| Lactose, fine powder | 1015 |
| Microcrystalline cellulose (AVICEL PH 102) | 1400 |
| Sodium carboxymethyl cellulose | 14 |
| Polyvinylpyrrolidon K 30 | 10 |

TABLE 8-continued

| possible sachet composition | |
|---|---|
| ingredient | mg/sachet |
| Magnesium stearate | 10 |
| Flavoring additives | 1 |
| Total | 2500 |

Manufacturing Procedure

The compound of formula I is mixed with lactose, microcrystalline cellulose and sodium carboxymethyl cellulose and granulated with a mixture of polyvinylpyrrolidone in water. The granulate is mixed with magnesium stearate and the flavoring additives and filled into sachets.

Experimental Part

The following examples are provided for illustration of the invention. They should not be considered as limiting the scope of the invention, but merely as being representative thereof.

Example 1

(2RS)-2-(6,7-Dihydro-5H-pyrrolo[1,2-c]imidazol-1-yl)-2-[4-fluoro-6-[2-[4-[(4-methylpiperazin-1-yl)methyl]phenyl]ethynyl]-1-oxo-isoindolin-2-yl]-N-thiazol-2-yl-acetamide Step 1: Ethyl 2-(6,7-dihydro-5H-pyrrolo[1,2-c]imidazol-1-yl)-2-oxo-acetate

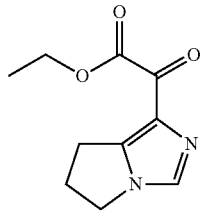

To a solution of ethyl 2-(6,7-dihydro-5H-pyrrolo[1,2-c]imidazol-1-yl)acetate (20.0 g, 102.97 mmol) dissolved in 200 ml of 1,4-dioxane was added selenium dioxide (22.85 g, 205.94 mmol, 2 equiv.). The reaction mixture was stirred for 5 hours at 80° C. The reaction mixture was concentrated under vacuum to give a residue. The crude product was purified by flash chromatography on a silica gel column eluting with petroleum ether:ethyl acetate 2:1 to ethyl acetate:ethanol 10:1 gradient to obtain the desired ethyl 2-(6,7-dihydro-5H-pyrrolo[1,2-c]imidazol-1-yl)-2-oxo-acetate (quant. yield) as a light brown oil, MS: m/e=209.1 (M+H$^+$).

Step 2: Ethyl 2-(6,7-dihydro-5H-pyrrolo[1,2-c]imidazol-1-yl)-2-hydroxyimino-acetate

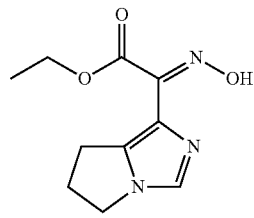 [SMILES: CCOC(=O)/C(=N/O)c1ncn2c1CCC2]

To a solution of ethyl 2-(6,7-dihydro-5H-pyrrolo[1,2-c]imidazol-1-yl)-2-oxo-acetate (Example 1, step 1) (17.5 g, 84.05 mmol) dissolved in 145 ml of ethanol was added hydroxylamine hydrochloride (6.42 g, 92.45 mmol, 1.1 equiv.) and sodium acetate (13.79 g, 168.1 mmol, 2 equiv.) at room temperature. The reaction mixture was stirred for 3.5 hours at 80° C. The reaction mixture was concentrated and extracted with water and five times with a mixture of ethanol/THF/ethyl acetate 1:1:8. The organic layers were concentrated to dryness. The desired ethyl 2-(6,7-dihydro-5H-pyrrolo[1,2-c]imidazol-1-yl)-2-hydroxyimino-acetate (15 g, 80% yield) was obtained as a yellow solid, MS: m/e=224.1 (M+H$^+$) and used directly in the next step.

Step 3: Ethyl (2RS)-2-amino-2-(6,7-dihydro-5H-pyrrolo[1,2-c]imidazol-1-yl)acetate

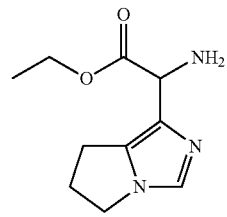

To a solution of ethyl 2-(6,7-dihydro-5H-pyrrolo[1,2-c]imidazol-1-yl)-2-hydroxyimino-acetate (Example 1, step 2) (15.0 g, 67.2 mmol) dissolved in 225 ml of ethanol and 120 ml of THF was added Pd/C (30.0 g, 67.2 mmol, 1 eq, 10%) at room temperature. The mixture was hydogenated with H$_2$ for 24 hours at 45° C. The reaction mixture was filtered and the filtrate was concentrated under vacuum. The desired ethyl (2RS)-2-amino-2-(6,7-dihydro-5H-pyrrolo[1,2-c]imidazol-1-yl)acetate (quant. yield) was obtained as a brown oil, MS: m/e=210.1 (M+H$^+$) and used directly in the next step.

Step 4: Ethyl (2RS)-2-amino-2-(6,7-dihydro-5H-pyrrolo[1,2-c]imidazol-1-yl)acetate hydrochloride

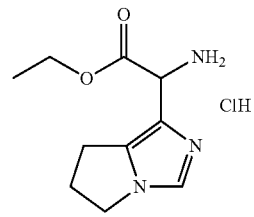

A solution of ethyl (2RS)-2-amino-2-(6,7-dihydro-5H-pyrrolo[1,2-c]imidazol-1-yl)acetate (Example 1, step 3) (15.0 g, 82.79 mmol) in HCl/EtOH (300 ml, 1200 mmol, 14.5 equiv., 2.5 mol/L) was stirred at 25° C. for 36 hours. The reaction mixture was concentrated under vacuum below 25°° C. to give a residue as brown oil. 150 ml of acetonitrile were added to the residue and the precipitated yellow solid was collected and dried under vacuum below 25° C. to give the desired ethyl (2RS)-2-amino-2-(6,7-dihydro-5H-pyrrolo[1,2-c]imidazol-1-yl)acetate hydrochloride (quant. yield) as yellow solid, MS: m/e=210.1 (M+H$^+$).

Step 5: Methyl
5-bromo-2-(bromomethyl)-3-fluoro-benzoate

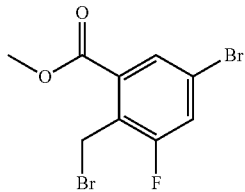

Methyl 5-bromo-3-fluoro-2-methylbenzoate (5.91 g, 23.9 mmol) was dissolved in 100 ml trifluorotoluene and N-bromosuccinimide (4.26 g, 23.9 mmol, 1 equiv.) and AIBN (393 mg, 2.39 mmol, 0.1 equiv.) were added at room temperature. The mixture was stirred at 110° C. for 3 hours. The reaction mixture was cooled, extracted with water and two times with ethyl acetate. The organic layers were dried over sodium sulfate and concentrated to dryness. The crude product was purified by flash chromatography on a silica gel column eluting with an ethyl acetate:heptane 0:100 to 50:50 gradient to obtain the desired methyl 5-bromo-2-(bromomethyl)-3-fluoro-benzoate (7.29 g, 94% yield) as a light yellow liquid, MS: m/e=326.8 (M+H$^+$).

Step 6: Ethyl (2RS)-2-(6-bromo-4-fluoro-1-oxo-isoindolin-2-yl)-2-(6,7-dihydro-5H-pyrrolo[1,2-c]imidazol-1-yl)acetate

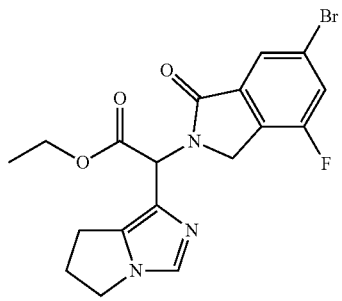 [SMILES: CCOC(=O)C(c1ncn2c1CCC2)N1Cc2c(F)cc(Br)cc2C1=O]

Ethyl (2RS)-2-amino-2-(6,7-dihydro-5H-pyrrolo[1,2-c]imidazol-1-yl)acetate hydrochloride (Example 1, step 4) (4.15 g, 16.9 mmol, 1 equiv.) was dissolved in 35 ml of DMF. Methyl 5-bromo-2-(bromomethyl)-3-fluoro-benzoate (Example 1, step 5) (5.0 g, 15.3 mmol) and triethylamine (10.7 ml, 76.7 mmol, 5 equiv.) were added at room temperature. The mixture was stirred at 80° C. for 16 hours. The reaction mixture was extracted with water and two times with ethyl acetate. The organic layers were extracted with brine, dried over sodium sulfate and concentrated to dryness. The crude product was purified by flash chromatography on a silica gel column eluting with a dichloromethane:methanol 100:0 to 90:10 gradient to obtain the desired ethyl (2RS)-2-(6-bromo-4-fluoro-1-oxo-isoindolin-2-yl)-2-(6,7-dihydro-5H-pyrrolo[1,2-c]imidazol-1-yl)acetate (2.6 g, 40% yield) as a yellow solid, MS: m/e=422.1/424.1 (M+H$^+$).

Step 7: Lithium ((2RS)-2-(6-bromo-4-fluoro-1-oxo-isoindolin-2-yl)-2-(6,7-dihydro-5H-pyrrolo[1,2-c]imidazol-1-yl)acetate

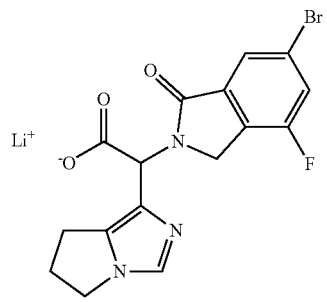

(2RS)-2-(6-Bromo-4-fluoro-1-oxo-isoindolin-2-yl)-2-(6,7-dihydro-5H-pyrrolo[1,2-c]imidazol-1-yl)acetate (Example 1, step 6) (1.96 g, 4.64 mmol) was dissolved in 16 ml of ethanol. LiOH (1M in water) (5.57 ml, 5.57 mmol, 1.2 equiv.) was added at room temperature. The mixture was stirred for 1 hour at room temperature. The reaction mixture was concentrated in vacuo to afford the desired crude lithium ((2RS)-2-(6-bromo-4-fluoro-1-oxo-isoindolin-2-yl)-2-(6,7-dihydro-5H-pyrrolo[1,2-c]imidazol-1-yl)acetate (1.92 g, quant.) as a light brown solid, MS: m/e=394.1/396.1 (M+H$^+$).

Step 8: (2RS)-2-(6-Bromo-4-fluoro-1-oxo-isoindolin-2-yl)-2-(6,7-dihydro-5H-pyrrolo[1,2-c]imidazol-1-yl)-N-thiazol-2-yl-acetamide

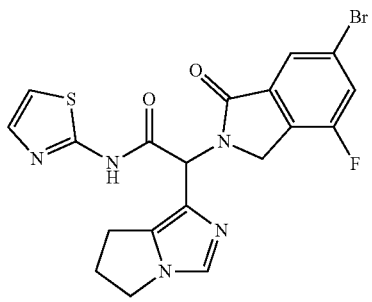 [SMILES: O=C(Nc1nccs1)C(c1ncn2c1CCC2)N1Cc2c(F)cc(Br)cc2C1=O]

Lithium ((2RS)-2-(6-bromo-4-fluoro-1-oxo-isoindolin-2-yl)-2-(6,7-dihydro-5H-pyrrolo[1,2-c]imidazol-1-yl)acetate (Example 1, step 7) (2.53 g, 6.32 mmol) was dissolved in 10 ml of DMF. Thiazol-2-amine (760 mg, 7.59 mmol, 1.2 equiv.), Hunig's base (5.5 ml, 31.6 mmol, 5 equiv.) and HATU (2.89 g, 7.59 mmol, 1.2 equiv.) were added at room temperature. The mixture was stirred at room temperature for 1 hour. The reaction mixture was extracted with water and two times with a 9:1 mixture of dichloromethane:methanol. The organic layers were extracted with water, dried over sodium sulfate and concentrated to dryness. The crude product was purified by flash chromatography on a silica gel column eluting with a dichloromethane:methanol 100:0 to 80:20 gradient to obtain the desired (2RS)-2-(6-bromo-4-fluoro-1-oxo-isoindolin-2-yl)-2-(6,7-dihydro-5H-pyrrolo[1,2-c]imidazol-1-yl)-N-thiazol-2-yl-acetamide (1.8 g, 60% yield) as a light brown solid, MS: m/e=476.1/478.1 (M+H$^+$).

Step 9: (2RS)-2-(6,7-Dihydro-5H-pyrrolo[1,2-c]imidazol-1-yl)-2-[4-fluoro-6-[2-(4-formylphenyl)ethynyl]-1-oxo-isoindolin-2-yl]-N-thiazol-2-yl-acetamide

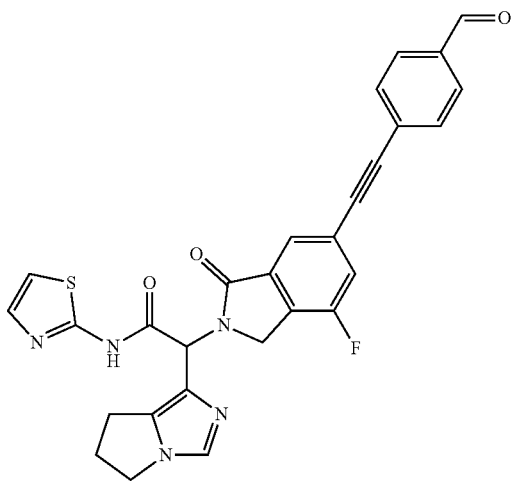 [SMILES: O=Cc1ccc(C#Cc2cc(F)c3c(c2)C(=O)N(C(C(=O)Nc2nccs2)c2ncn4c2CCC4)C3)cc1]

(2RS)-2-(6-Bromo-4-fluoro-1-oxo-isoindolin-2-yl)-2-(6,7-dihydro-5H-pyrrolo[1,2-c]imidazol-1-yl)-N-thiazol-2-yl-acetamide (Example 1, step 8) (140 mg, 0.29 mmol) and 4-ethynylbenzaldehyde (49.7 mg, 0.382 mmol, 1.3 equiv.) were dissolved in 12 ml of DMF. triethylamine (89 mg, 0.123 ml, 0.882 mmol, 3 equiv.), bis-(triphenylphosphine)-palladium(II)dichloride (10 mg, 0.015 mmol, 0.05 equiv.), triphenylphosphine (8 mg, 0.03 mmol, 0.1 equiv.) and copper(I) iodide (3 mg, 0.015 mmol, 0.05 equiv.) were added and the mixture was stirred for 4 hours at 80° C. The reaction mixture was extracted with water and two times with ethyl acetate. The organic layers were extracted with brine, dried over sodium sulfate and concentrated to dryness. The crude product was purified by flash chromatography on a silica gel column eluting with a dichloromethane:methanol 100:0 to 90:10 gradient to obtain the desired (2RS)-2-(6,7-dihydro-5H-pyrrolo[1,2-c]imidazol-1-yl)-2-[4-fluoro-6-[2-(4-formylphenyl)ethynyl]-1-oxo-isoindolin-2-yl]-N-thiazol-2-yl-acetamide (130 mg, 86% yield) as a yellow solid, MS: m/e=526.1 (M+H$^+$).

Step 10: (2RS)-2-(6,7-Dihydro-5H-pyrrolo[1,2-c]imidazol-1-yl)-2-[4-fluoro-6-[2-[4-[(4-methylpiperazin-1-yl)methyl]phenyl]ethynyl]-1-oxo-isoindolin-2-yl]-N-thiazol-2-yl-acetamide (2RS)-2-(6,7-Dihydro-5H-pyrrolo[1,2-c]imidazol-1-yl)-2-[4-fluoro-6-[2-(4-formylphenyl)ethynyl]-1-oxo-isoindolin-2-yl]-N-thiazol-2-yl-acetamide (Example 1, step 9) (40 mg, 0.076 mmol) was dissolved in 1 ml of dichloromethane. 1-Methylpiperazine (11 mg, 0.114 mmol, 1.5 equiv.) and sodium triacetoxyhydroborate (24 mg, 0.114 mmol, 1.5 equiv.) were added at room temperature. The mixture was stirred at room temperature for 16 hours. The reaction mixture was extracted with water and two times with dichloromethane. The organic layers were extracted with brine, dried over sodium sulfate and concentrated to dryness. The crude product was purified by flash chromatography on a silica gel column eluting with a dichloromethane:methanol 100:0 to 85:15 gradient to obtain the desired (2RS)-2-(6,7-dihydro-5H-pyrrolo[1,2-c]imidazol-1-yl)-2-[4-fluoro-6-[2-[4-[(4-methylpiperazin-1-yl)methyl]phenyl]ethynyl]-1-oxo-isoindolin-2-yl]-N-thiazol-2-yl-acetamide (17 mg, 37% yield) as a white solid, MS: m/e=610.4 (M+H$^+$).

Example 2

(2RS)-2-(6,7-Dihydro-5H-pyrrolo[1,2-c]imidazol-1-yl)-2-[4-fluoro-6-[2-[4-[(4-hydroxy-1-piperidyl)methyl]phenyl]ethynyl]-1-oxo-isoindolin-2-yl]-N-thiazol-2-yl-acetamide The title compound was obtained as a white solid, MS: m/e=611.3 (M+H$^+$), using chemistry similar to that described in Example 1, step 10 starting from (2RS)-2-(6,7-Dihydro-5H-pyrrolo[1,2-c]imidazol-1-yl)-2-[4-fluoro-6-[2-(4-formylphenyl)ethynyl]-1-oxo-isoindolin-2-yl]-N-thiazol-2-yl-acetamide (Example 1, step 9) and piperidin-4-ol.

Example 3

(2RS)-2-(6,7-Dihydro-5H-pyrrolo[1,2-c]imidazol-1-yl)-2-[4-fluoro-1-oxo-6-(4-piperazin-1-ylphenyl)isoindolin-2-yl]-N-thiazol-2-yl-acetamide

Step 1: tert-Butyl 4-[4-[7-fluoro-3-oxo-2-[(1RS)-1-(6,7-dihydro-5H-pyrrolo[1,2-c]imidazol-1-yl)-2-ethoxy-2-oxo-ethyl]isoindolin-5-yl]phenyl]piperazine-1-carboxylate

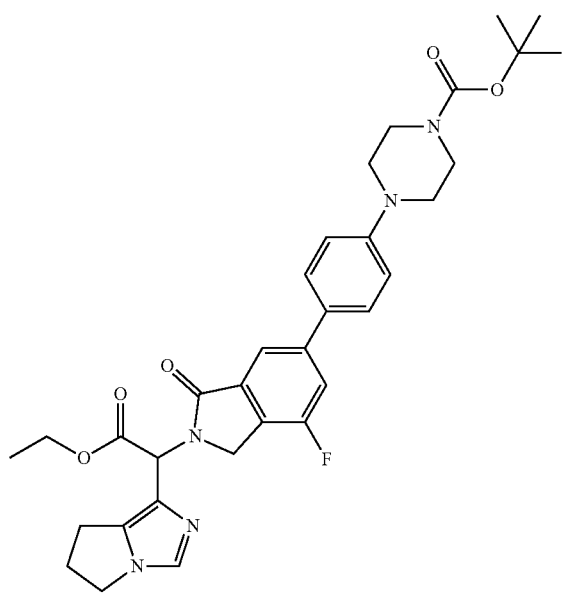

Ethyl (2RS)-2-(6-bromo-4-fluoro-1-oxo-isoindolin-2-yl)-2-(6,7-dihydro-5H-pyrrolo[1,2-c]imidazol-1-yl)acetate (Example 1, step 6) (56 mg, 0.133 mmol) and (4-(4-(tert-butoxycarbonyl)piperazin-1-yl)phenyl)boronic acid (41 mg, 0.133 mmol, 1.0 equiv.) were dissolved in 1.0 ml of 1,2-dimethoxyethane and 2M aq. Na$_2$CO$_3$-solution (0.199 ml, 0.398 mmol, 3.0 equiv.). Tetrakis(triphenylphosphine)palladium (0) (15 mg, 0.0133 mmol, 0.1 equiv.) was added and the reaction mixture was stirred at 80° C. for 4 hours. The reaction mixture was cooled to room temperature and then extracted with ethyl acetate and saturated NaHCO$_3$-solution. The aqueous layer was back-extracted with ethyl acetate. The organic layers were washed with water and brine. The organic layers were combined, dried over sodium sulfate, filtered and concentrated to dryness. The crude product was purified by flash chromatography on a silica gel column eluting with an ethyl acetate:heptane 5:95 to 100:0 gradient. The desired tert-butyl 4-[4-[7-fluoro-3-oxo-2-[(1RS)-1-(6,7-dihydro-5H-pyrrolo[1,2-c]imidazol-1-yl)-2-ethoxy-2-oxo-ethyl]isoindolin-5-yl]phenyl]piperazine-1-carboxylate (48 mg, 60% yield) was obtained as a light brown oil, MS: m/e=604.4 (M+H$^+$).

Step 2: tert-Butyl 4-[4-[7-fluoro-3-oxo-2-[(1RS)-1-(6,7-dihydro-5H-pyrrolo[1,2-c]imidazol-1-yl)-2-oxo-2-(thiazol-2-ylamino)ethyl]isoindolin-5-yl]phenyl]piperazine-1-carboxylate

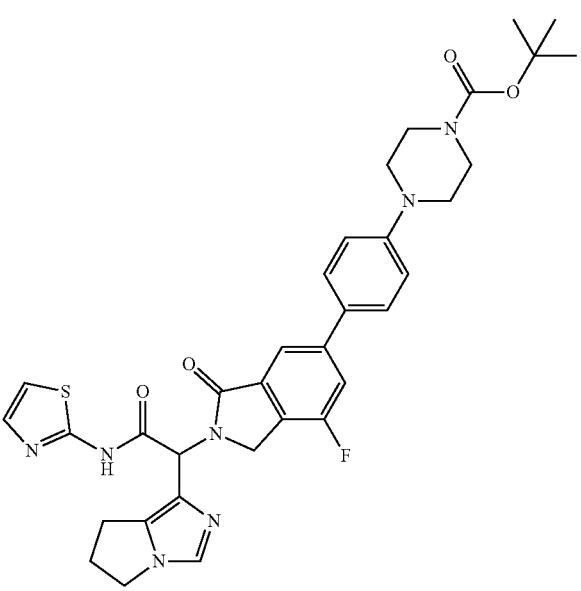

tert-Butyl 4-[4-[7-fluoro-3-oxo-2-[(1RS)-1-(6,7-dihydro-5H-pyrrolo[1,2-c]imidazol-1-yl)-2-ethoxy-2-oxo-ethyl]isoindolin-5-yl]phenyl]piperazine-1-carboxylate (Example 3, step 1) (48 mg, 0.0795 mmol) was combined with 11 ml of ethanol to give a light yellow solution. LiOH (1M in water) (0.0954 ml, 0.0954 mmol, 1.2 equiv.) was added. The reaction mixture was stirred at room temperature for 2 hours. The reaction mixture was concentrated in vacuo. The residue was taken up in ethanol and concentrated in vacuo and then dissolved in 7 ml of DMF. Thiazol-2-amine (9.55 mg, 0.0954 mmol, 1.2 equiv.) and Hunig's base (0.0694 ml, 0.398 mmol, 5 equiv.) were added followed by HATU (36.3 mg, 0.0954 mmol, 1.2 equiv.). The mixture was stirred at room temperature for 1 hour. The reaction mixture was extracted with ethyl acetate and saturated NaHCO$_3$-solution. The aqueous layer was back-extracted with ethyl acetate. The organic layers were washed with water and brine. The organic layers were combined, dried over sodium sulfate, filtered and concentrated to dryness. The crude product was purified by flash chromatography on a silica gel column eluting with a dichloromethane:methanol 100:0 to 90:10 gradient to obtain the desired tert-butyl 4-[4-[7-fluoro-3-oxo-2-[(1RS)-1-(6,7-dihydro-5H-pyrrolo[1,2-c]imidazol-1-yl)-2-oxo-2-(thiazol-2-ylamino)ethyl]isoindolin-5-yl]phenyl]piperazine-1-carboxylate (22 mg, 42% yield) as a yellow oil, MS: m/e=658.3 (M+H$^+$).

Step 3: (2RS)-2-(6,7-Dihydro-5H-pyrrolo[1,2-c] imidazol-1-yl)-2-[4-fluoro-1-oxo-6-(4-piperazin-1-ylphenyl)isoindolin-2-yl]-N-thiazol-2-yl-acetamide

Example 4

(2RS)-2-(6,7-Dihydro-5H-pyrrolo[1,2-c]imidazol-1-yl)-2-[6-[6-(4-ethylpiperazin-1-yl)-3-pyridyl]-4-fluoro-1-oxo-isoindolin-2-yl]-N-thiazol-2-yl-acetamide Step 1: tert-Butyl 4-[5-[7-fluoro-3-oxo-2-[(1RS)-1-(6,7-dihydro-5H-pyrrolo[1,2-c]imidazol-1-yl)-2-ethoxy-2-oxo-ethyl]isoindolin-5-yl]-2-pyridyl]piperazine-1-carboxylate

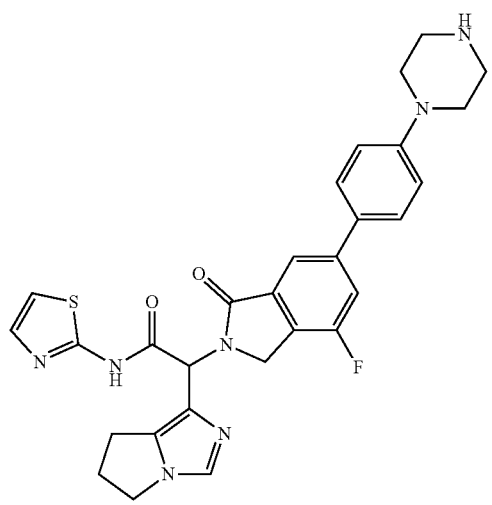 [SMILES: O=C(Nc1nccs1)C(c1ncn2c1CCC2)N1Cc2c(F)cc(-c3ccc(N4CCNCC4)cc3)cc2C1=O]

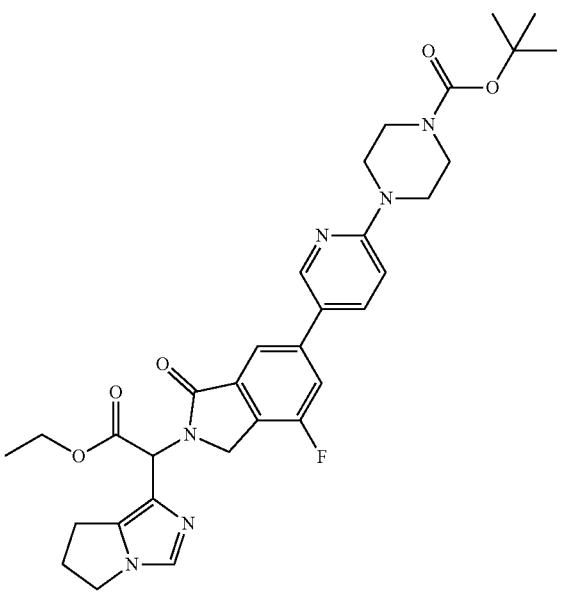 [SMILES: CCOC(=O)C(c1ncn2c1CCC2)N1Cc2c(F)cc(-c3ccc(N4CCN(C(=O)OC(C)(C)C)CC4)nc3)cc2C1=O]

tert-Butyl 4-[4-[7-fluoro-3-oxo-2-[(1RS)-1-(6,7-dihydro-5H-pyrrolo[1,2-c]imidazol-1-yl)-2-oxo-2-(thiazol-2-ylamino)ethyl]isoindolin-5-yl]phenyl]piperazine-1-carboxylate (Example 3, step 2) (26 mg, 0.0395 mmol) was [dissolved/suspended] in 0.5 ml of dichloromethane and 0.25 ml of methanol. HCl (4 M in dioxane) (0.099 ml, 0.395 mmol, 10 equiv.) was added at room temperature and the reaction mixture was stirred at room temperature for 16 hours. The reaction mixture was extracted with saturated NaHCO$_3$-solution and twice with dichloromethane. The organic layers were combined, dried over sodium sulfate, filtered and concentrated to dryness. The desired (2RS)-2-(6,7-dihydro-5H-pyrrolo[1,2-c]imidazol-1-yl)-2-[4-fluoro-1-oxo-6-(4-piperazin-1-ylphenyl)isoindolin-2-yl]-N-thiazol-2-yl-acetamide (22 mg, 99.8% yield) was obtained as a light yellow oil, MS: m/e=558.2 (M+H$^+$).

The title compound was obtained as a brown oil, MS: m/e=605.3 (M+H$^+$), using chemistry similar to that described in Example 3, step 1 starting from ethyl (2RS)-2-(6-bromo-4-fluoro-1-oxo-isoindolin-2-yl)-2-(6,7-dihydro-5H-pyrrolo[1,2-c]imidazol-1-yl)acetate (Example 1, step 6) and (6-(4-(tert-butoxycarbonyl)piperazin-1-yl)pyridin-3-yl)boronic acid.

Step 2: tert-Butyl 4-[5-[7-fluoro-3-oxo-2-[(1RS)-1-(6,7-dihydro-5H-pyrrolo[1,2-c]imidazol-1-yl)-2-oxo-2-(thiazol-2-ylamino)ethyl]isoindolin-5-yl]-2-pyridyl]piperazine-1-carboxylate

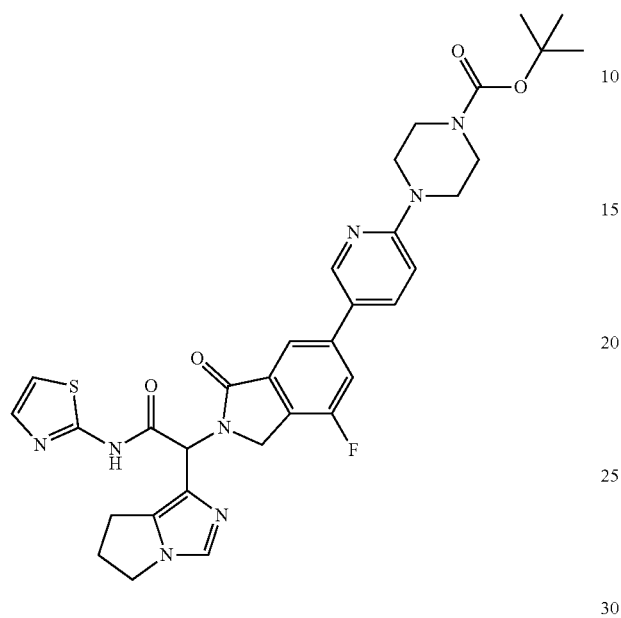

The title compound was obtained as a yellow oil, MS: m/e=659.1 (M+H⁺), using chemistry similar to that described in Example 3, step 2 starting from tert-butyl 4-[5-[7-fluoro-3-oxo-2-[(1RS)-1-(6,7-dihydro-5H-pyrrolo[1,2-c]imidazol-1-yl)-2-ethoxy-2-oxo-ethyl]isoindolin-5-yl]-2-pyridyl]piperazine-1-carboxylate (Example 4, step 1) and thiazol-2-amine.

Step 3: (2RS)-2-(6,7-Dihydro-5H-pyrrolo[1,2-c]imidazol-1-yl)-2-[4-fluoro-1-oxo-6-(6-piperazin-1-yl-3-pyridyl)isoindolin-2-yl]-N-thiazol-2-yl-acetamide

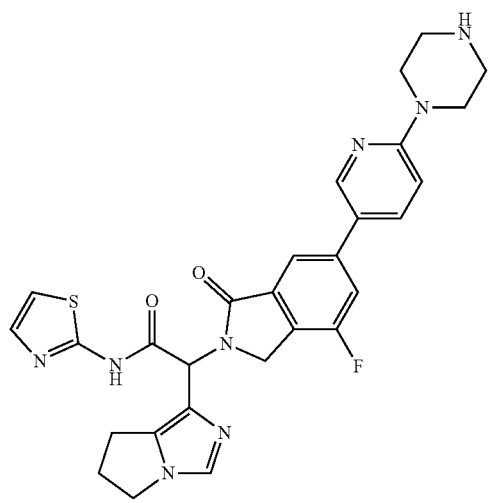 [SMILES: O=C(Nc1nccs1)C(c1ncn2c1CCC2)N1Cc2c(F)cc(-c3ccc(N4CCNCC4)nc3)cc2C1=O]

The title compound was obtained as a light brown solid, MS: m/e=559.1 (M+H⁺), using chemistry similar to that described in Example 3, step 3 starting from tert-butyl 4-[5-[7-fluoro-3-oxo-2-[(1RS)-1-(6,7-dihydro-5H-pyrrolo[1,2-c]imidazol-1-yl)-2-oxo-2-(thiazol-2-ylamino)ethyl]isoindolin-5-yl]-2-pyridyl]piperazine-1-carboxylate (Example 4, step 2).

Step 4: (2RS)-2-(6,7-Dihydro-5H-pyrrolo[1,2-c]imidazol-1-yl)-2-[6-[6-(4-ethylpiperazin-1-yl)-3-pyridyl]-4-fluoro-1-oxo-isoindolin-2-yl]-N-thiazol-2-yl-acetamide

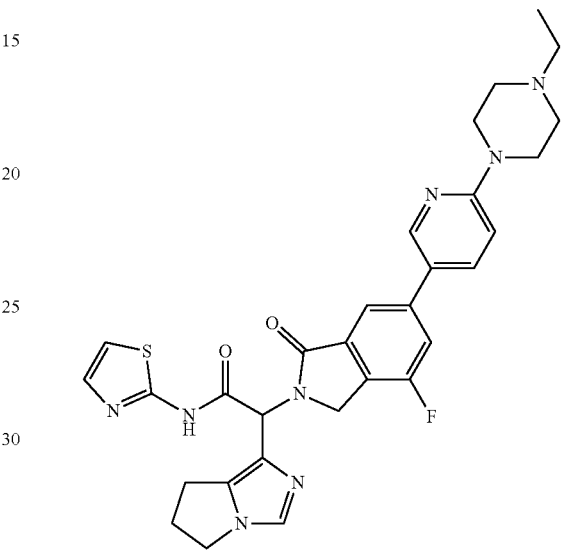

(2RS)-2-(6,7-Dihydro-5H-pyrrolo[1,2-c]imidazol-1-yl)-2-[4-fluoro-1-oxo-6-(6-piperazin-1-yl-3-pyridyl)isoindolin-2-yl]-N-thiazol-2-yl-acetamide (Example 4, step 3) (45 mg, 0.0806 mmol) was dissolved in 1.0 ml of DMF. Ethyl iodide (13.8 mg, 7.16 µl, 0.0886 mmol, 1.1 equiv.) and Hunig's base (41.6 mg, 56.3 µl, 0.322 mmol, 4 equiv.) were added at room temperature. The reaction mixture was stirred at 60° ° C. for 1 hour. The reaction mixture was cooled to room temperature and then extracted with ethyl acetate and water. The aqueous layer was back-extracted with ethyl acetate. The organic layers were washed with brine. The organic layers were combined, dried over sodium sulfate, filtered and concentrated to dryness. The crude product was purified by flash chromatography on a silica gel column eluting with a dichloromethane:methanol 100:0 to 85:15 gradient to obtain the desired (2RS)-2-(6,7-dihydro-5H-pyrrolo[1,2-c]imidazol-1-yl)-2-[6-[6-(4-ethylpiperazin-1-yl)-3-pyridyl]-4-fluoro-1-oxo-isoindolin-2-yl]-N-thiazol-2-yl-acetamide (24 mg, 51% yield) as a light yellow solid, MS: m/e=587.3 (M+H⁺).

Example 5

(2RS)-2-(6,7-Dihydro-5H-pyrrolo[1,2-c]imidazol-1-yl)-2-[6-[4-(4-ethylpiperazin-1-yl)phenyl]-4-fluoro-1-oxo-isoindolin-2-yl]-N-thiazol-2-yl-acetamide The title compound was obtained as a light yellow solid, MS: m/e=586.3 (M+H⁺), using chemistry similar to that described in Example 4, step 4 starting from (2RS)-2-(6,7-dihydro-5H-pyrrolo[1,2-c]imidazol-1-yl)-2-[4-fluoro-1- oxo-6-(4-piperazin-1-ylphenyl)isoindolin-2-yl]-N-thiazol-2-yl-acetamide (Example 3, step 3) and ethyl iodide.

Example 6

(2RS)-2-[4-Chloro-6-[4-(4-ethylpiperazin-1-yl)phenyl]-1-oxo-isoindolin-2-yl]-2-(6,7-dihydro-5H-pyrrolo[1,2-c]imidazol-1-yl)-N-thiazol-2-yl-acetamide Step 1: Methyl 5-bromo-2-(bromomethyl)-3-chloro-benzoate

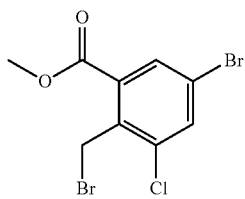

The title compound was obtained as a colorless solid, MS: m/e=343.4 (M+H$^+$), using chemistry similar to that described in Example 1, step 5 starting from methyl 5-bromo-3-chloro-2-methyl-benzoate.

Step 2: Ethyl (2RS)-2-(6-bromo-4-chloro-1-oxo-isoindolin-2-yl)-2-(6,7-dihydro-5H-pyrrolo[1,2-c]imidazol-1-yl)acetate

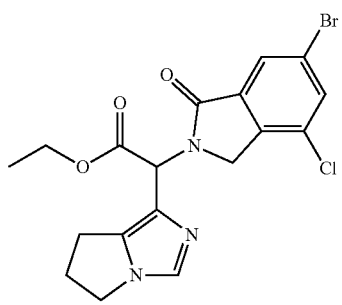 [SMILES: CCOC(=O)C(c1ncn2c1CCC2)N1Cc2c(Cl)cc(Br)cc2C1=O]

The title compound was obtained as a red amorphous, MS: m/e=438.0/440.0 (M+H$^+$), using chemistry similar to that described in Example 1, step 6 starting from ethyl (2RS)-2-amino-2-(6,7-dihydro-5H-pyrrolo[1,2-c]imidazol-1-yl)acetate (Example 1, step 3) and methyl 5-bromo-2-(bromomethyl)-3-chloro-benzoate (Example 6, step 1).

Step 3: Ethyl (2RS)-2-[4-chloro-6-[4-(4-ethylpiperazin-1-yl)phenyl]-1-oxo-isoindolin-2-yl]-2-(6,7-dihydro-5H-pyrrolo[1,2-c]imidazol-1-yl)acetate

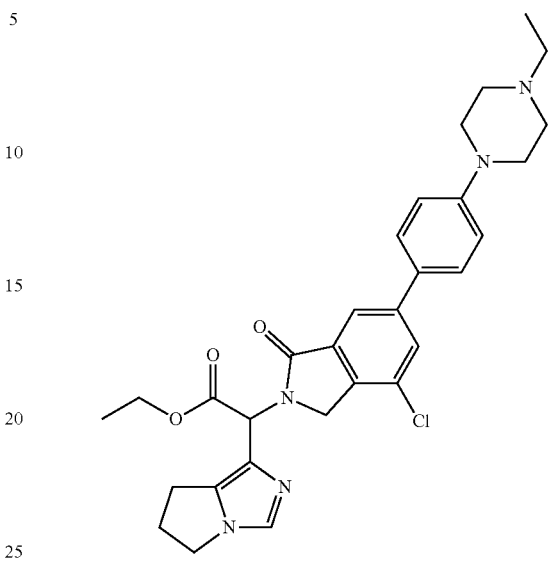

The title compound was obtained as an off-white amorphous, MS: m/e=548.3 (M+H$^+$), using chemistry similar to that described in Example 3, step 1 starting from ethyl (2RS)-2-(6-bromo-4-chloro-1-oxo-isoindolin-2-yl)-2-(6,7-dihydro-5H-pyrrolo[1,2-c]imidazol-1-yl)acetate (Example 6, step 2) and 1-ethyl-4-[4-(4,4,5,5-tetramethyl-1,3,2-dioxaborolan-2-yl)phenyl]piperazine.

Step 4: (2RS)-2-[4-Chloro-6-[4-(4-ethylpiperazin-1-yl)phenyl]-1-oxo-isoindolin-2-yl]-2-(6,7-dihydro-5H-pyrrolo[1,2-c]imidazol-1-yl)-N-thiazol-2-yl-acetamide

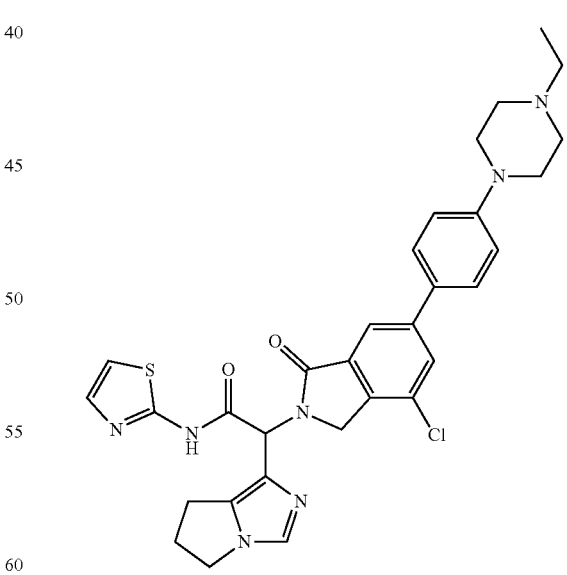

The title compound was obtained as a light yellow solid, MS: m/e=602.2 (M+H$^+$), using chemistry similar to that described in Example 3, step 2 starting from ethyl (2RS)-2-[4-chloro-6-[4-(4-ethylpiperazin-1-yl)phenyl]-1-oxo-isoindolin-2-yl]-2-(6,7-dihydro-5H-pyrrolo[1,2-c]imidazol-1-yl)acetate (Example 6, step 3) and thiazol-2-amine.

Example 7

(2RS)-2-(6,7-Dihydro-5H-pyrrolo[1,2-c]imidazol-1-yl)-2-[4-fluoro-6-[4-(4-hydroxy-1-piperidyl)phenyl]-1-oxo-isoindolin-2-yl]-N-thiazol-2-yl-acetamide Step 1: Ethyl (2RS)-2-(6,7-dihydro-5H-pyrrolo[1,2-c]imidazol-1-yl)-2-[4-fluoro-6-[4-(4-hydroxy-1-piperidyl)phenyl]-1-oxo-isoindolin-2-yl]acetate

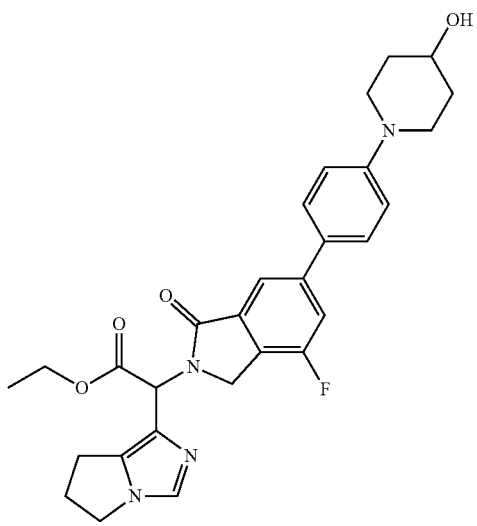 [SMILES: CCOC(=O)C(c1ncn2c1CCC2)N1Cc2c(F)cc(-c3ccc(N4CCC(O)CC4)cc3)cc2C1=O]

The title compound was obtained as a yellow solid, MS: m/e=519.2 (M+H⁺), using chemistry similar to that described in Example 3, step 1 starting from ethyl (2RS)-2-(6-bromo-4-fluoro-1-oxo-isoindolin-2-yl)-2-(6,7-dihydro-5H-pyrrolo[1,2-c]imidazol-1-yl)acetate (Example 1, step 6) and 1-[4-(4,4,5,5-tetramethyl-1,3,2-dioxaborolan-2-yl)phenyl]piperidin-4-ol.

Step 2: (2RS)-2-(6,7-Dihydro-5H-pyrrolo[1,2-c]imidazol-1-yl)-2-[4-fluoro-6-[4-(4-hydroxy-1-piperidyl)phenyl]-1-oxo-isoindolin-2-yl]-N-thiazol-2-yl-acetamide

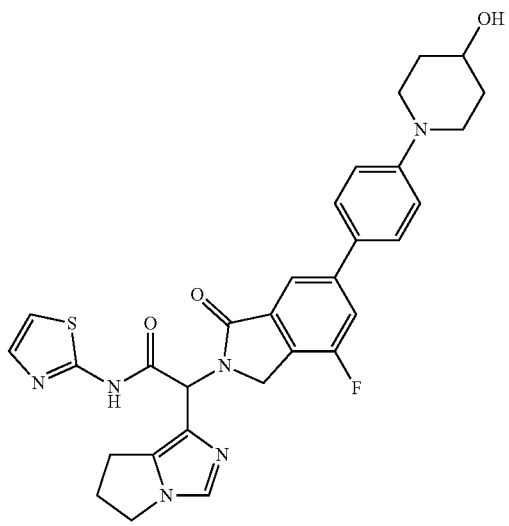 [SMILES: O=C(Nc1nccs1)C(c1ncn2c1CCC2)N1Cc2c(F)cc(-c3ccc(N4CCC(O)CC4)cc3)cc2C1=O]

The title compound was obtained as a light brown solid, MS: m/e=573.1 (M+H⁺), using chemistry similar to that described in Example 3, step 2 starting from ethyl (2RS)-2-(6,7-dihydro-5H-pyrrolo[1,2-c]imidazol-1-yl)-2-[4-fluoro-6-[4-(4-hydroxy-1-piperidyl)phenyl]-1-oxo-isoindolin-2-yl]acetate (Example 7, step 1) and thiazol-2-amine.

Example 8

(2RS)-2-[4-Chloro-6-[6-(4-hydroxy-1-piperidyl)-3-pyridyl]-1-oxo-isoindolin-2-yl]-2-(6,7-dihydro-5H-pyrrolo[1,2-c]imidazol-1-yl)-N-thiazol-2-yl-acetamide Step 1: (2RS)-2-(6,7-Dihydro-5H-pyrrolo[1,2-c]imidazol-1-yl)-2-[4-fluoro-6-[6-(4-hydroxy-1-piperidyl)-3-pyridyl]-1-oxo-isoindolin-2-yl]acetic acid

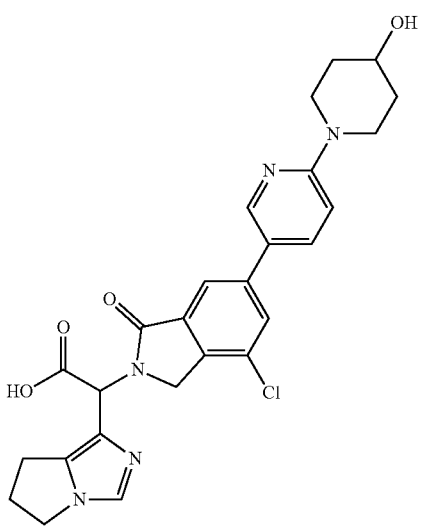 [SMILES: O=C(O)C(c1ncn2c1CCC2)N1Cc2c(Cl)cc(-c3ccc(N4CCC(O)CC4)nc3)cc2C1=O]

The title compound was obtained as a dark grey solid, MS: m/e=508.3/510.3 (M+H⁺), using chemistry similar to that described in Example 3, step 1 starting from ethyl (2RS)-2-(6-bromo-4-fluoro-1-oxo-isoindolin-2-yl)-2-(6,7-dihydro-5H-pyrrolo[1,2-c]imidazol-1-yl)acetate (Example 1, step 6) and (6-(4-hydroxypiperidin-1-yl)pyridin-3-yl)boronic acid by isolating the formed corresponding acid.

Step 2: (2RS)-2-[4-Chloro-6-[6-(4-hydroxy-1-piperidyl)-3-pyridyl]-1-oxo-isoindolin-2-yl]-2-(6,7-dihydro-5H-pyrrolo[1,2-c]imidazol-1-yl)-N-thiazol-2-yl-acetamide

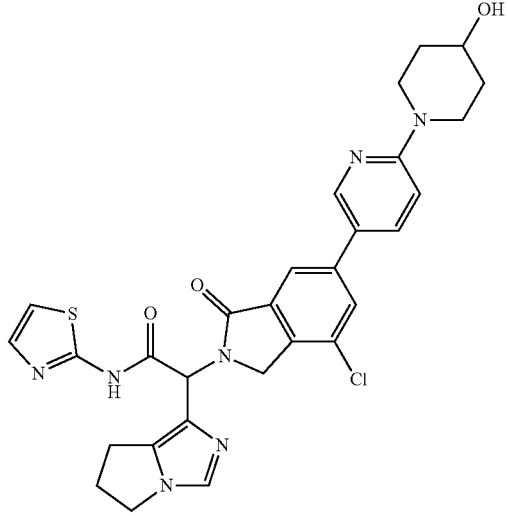

The title compound was obtained as a light brown solid, MS: m/e=590.1/592.1 (M+H⁺), using chemistry similar to that described in Example 1, step 8 starting from (2RS)-2-(6,7-dihydro-5H-pyrrolo[1,2-c]imidazol-1-yl)-2-[4-fluoro-6-[6-(4-hydroxy-1-piperidyl)-3-pyridyl]-1-oxo-isoindolin-2-yl]acetic acid (Example 8, step 1) and thiazol-2-amine.

Example 9

(2RS)-2-[4-Chloro-6-[2-[4-[(4-hydroxy-1-piperidyl)methyl]phenyl]ethynyl]-1-oxo-isoindolin-2-yl]-2-(6,7-dihydro-5H-pyrrolo[1,2-c]imidazol-1-yl)-N-thiazol-2-yl-acetamide Step 1: 1-[(4-Ethynylphenyl)methyl]piperidin-4-ol

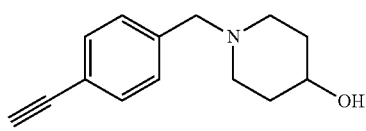 [SMILES: C#Cc1ccc(CN2CCC(O)CC2)cc1]

The title compound was obtained as a yellow solid, MS: m/e=216.2 (M+H⁺), using chemistry similar to that described in Example 1, step 10 starting from 4-ethynyl-benzaldehyde and piperidin-4-ol.

Step 2: Methyl 3-chloro-5-iodo-2-methyl-benzoate

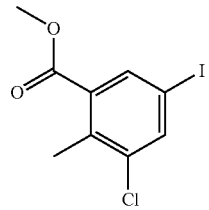

3-Chloro-5-iodo-2-methyl-benzoic acid (1 g, 3.37 mmol) was dissolved in 20 ml of methanol and sulfuric acid (33.1 mg, 0.018 ml, 0.337 mmol, 0.1 equiv.) was added at room temperature. The mixture was stirred at 70° C. for 4 hours. Sulfuric acid (0.18 ml, 3.37 mmol, 1.0 equiv.) was added and the mixture was stirred at 80° ° C. for 16 hours. The reaction mixture was concentrated to a volume of ~5 ml and then extracted with ethyl acetate and saturated NaHCO₃-solution. The aqueous layer was back-extracted with ethyl acetate. The organic layers were washed with water. The organic layers were combined, dried over sodium sulfate, filtered and concentrated on Isolute® to dryness. The crude product was purified by flash chromatography on a silica gel column eluting with an ethyl acetate:heptane 0:100 to 50:50 gradient. The desired methyl 3-chloro-5-iodo-2-methyl-benzoate (941 mg, 90% yield) was obtained as a white solid, MS: m/e=309.1 (M−H⁻).

Step 3: Methyl 2-(bromomethyl)-3-chloro-5-iodo-benzoate

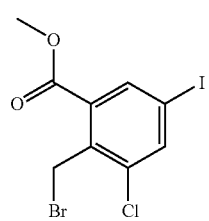

The title compound was obtained as a white solid, MS: m/e=388.4 (M−H⁻), using chemistry similar to that described in Example 1, step 5 starting from methyl 3-chloro-5-iodo-2-methyl-benzoate (Example 9, step 2).

Step 4: Ethyl (2RS)-2-(4-chloro-6-iodo-1-oxo-isoindolin-2-yl)-2-(6,7-dihydro-5H-pyrrolo[1,2-c]imidazol-1-yl)acetate

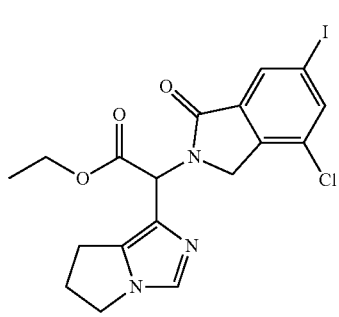 [SMILES: CCOC(=O)C(c1ncn2c1CCC2)N1Cc2c(Cl)cc(I)cc2C1=O]

The title compound was obtained as a dark brown semi-solid, MS: m/e=486.1/488.0 (M+H+), using chemistry similar to that described in Example 1, step 6 starting from ethyl (2RS)-2-amino-2-(6,7-dihydro-5H-pyrrolo[1,2-c]imidazol-1-yl)acetate hydrochloride (Example 1, step 4) and methyl 2-(bromomethyl)-3-chloro-5-iodo-benzoate (Example 9, step 3).

Step 5: Ethyl (2RS)-2-[4-chloro-6-[2-[4-[(4-hydroxy-1-piperidyl)methyl]phenyl]ethynyl]-1-oxo-isoindolin-2-yl]-2-(6,7-dihydro-5H-pyrrolo[1,2-c]imidazol-1-yl)acetate

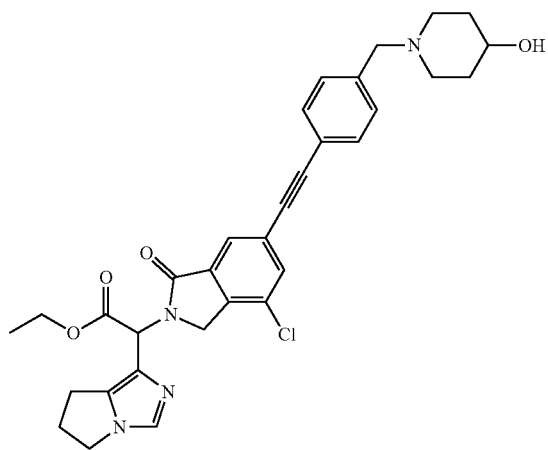 [SMILES: CCOC(=O)C(c1ncn2c1CCC2)N1Cc2c(Cl)cc(C#Cc3ccc(CN4CCC(O)CC4)cc3)cc2C1=O]

The title compound was obtained as a yellow solid, MS: m/e=573.2/575.2 (M+H+), using chemistry similar to that described in Example 1, step 9 starting from ethyl (2RS)-2-(4-chloro-6-iodo-1-oxo-isoindolin-2-yl)-2-(6,7-dihydro-5H-pyrrolo[1,2-c]imidazol-1-yl)acetate (Example 9, step 4) and 1-[(4-ethynylphenyl)methyl]piperidin-4-ol (Example 9, step 1).

Step 6: (2RS)-2-[4-Chloro-6-[2-[4-[(4-hydroxy-1-piperidyl)methyl]phenyl]ethynyl]-1-oxo-isoindolin-2-yl]-2-(6,7-dihydro-5H-pyrrolo[1,2-c]imidazol-1-yl)-N-thiazol-2-yl-acetamide

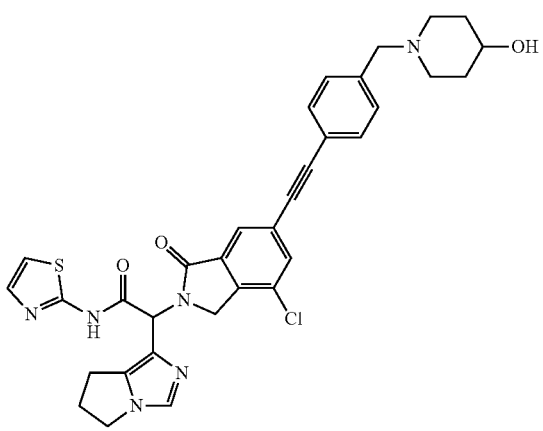 [SMILES: O=C(Nc1nccs1)C(c1ncn2c1CCC2)N1Cc2c(Cl)cc(C#Cc3ccc(CN4CCC(O)CC4)cc3)cc2C1=O]

The title compound was obtained as a light yellow solid, MS: m/e=627.5/629.5 (M+H+), using chemistry similar to that described in Example 3, step 2 starting from ethyl (2RS)-2-[4-chloro-6-[2-[4-[(4-hydroxy-1-piperidyl)methyl]phenyl]ethynyl]-1-oxo-isoindolin-2-yl]-2-(6,7-dihydro-5H-pyrrolo[1,2-c]imidazol-1-yl)acetate (Example 9, step 5) and thiazol-2-amine.

Example 10

(2RS)-2-(6,7-Dihydro-5H-pyrrolizin-1-yl)-2-[4-fluoro-6-[2-[4-[(4-hydroxy-1-piperidyl)methyl]phenyl]ethynyl]-1-oxo-isoindolin-2-yl]-N-thiazol-2-yl-acetamide Step 1: Methyl 5-bromo-3-fluoro-2-(3,5,7-triaza-1-azoniatricyclo[3.3.1.13,7]decan-1-ylmethyl)benzoate bromide

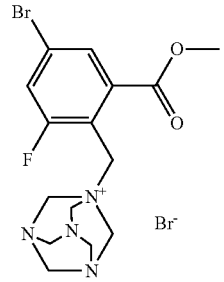 [SMILES: COC(=O)c1cc(Br)cc(F)c1C[N+]12CN3CN(CN(C3)C1)C2 ; [Br-]]

Methyl 5-bromo-2-(bromomethyl)-3-fluoro-benzoate (Example 1, step 4) (300 mg, 0.920 mmol) was dissolved in 5 ml of chloroform and 1,3,5,7-tetrazatricyclo[3.3.1.13,7]decane (135 mg, 0.966 mmol, 1.05 equiv.) was added at room temperature. The reaction mixture was stirred at 70° C. for 2 hours. The resulting suspension was filtered and washed two times with dichloromethane. The filter cake was dried to afford the desired methyl 5-bromo-3-fluoro-2-(3,5,7-triaza-1-azoniatricyclo[3.3.1.13,7]decan-1-ylmethyl)benzoate bromide (369 mg, 86% yield) as a white solid, MS: m/e=385.2/387.2 (M+H+).

Step 2: Methyl 2-(aminomethyl)-5-bromo-3-fluoro-benzoate hydrochloride

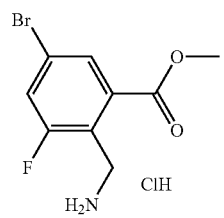

Methyl 5-bromo-3-fluoro-2-(3,5,7-triaza-1-azoniatricyclo[3.3.1.13,7]decan-1-ylmethyl)benzoate bromide (Example 10, step 1) (369 mg, 0.792 mmol) was suspended in 5 ml of methanol and HCl (25% in water) (0.618 ml, 4.75 mmol, 6 equiv.) was added at room temperature. The reaction mixture was stirred at 75° C. for 2 hours. The reaction mixture was concentrated to dryness and used without further purification. The desired methyl 2-(aminomethyl)-5- bromo-3-fluoro-benzoate hydrochloride (393 mg, quantitative, 60% purity) was obtained as a white solid, MS: m/e=262.1 (M–H⁻).

Step 3: (2RS)-2-(6-Bromo-4-fluoro-1-oxo-isoindolin-2-yl)-2-(6,7-dihydro-5H-pyrrolizin-1-yl)acetonitrile

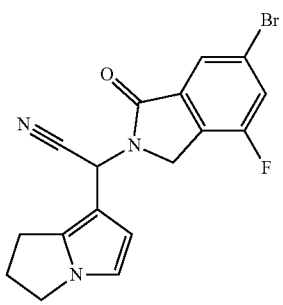 [SMILES: N#CC(c1ccn2c1CCC2)N1Cc2c(F)cc(Br)cc2C1=O]

A mixture of 6,7-dihydro-5H-pyrrolizine-1-carbaldehyde (100 mg, 0.740 mmol), methyl 2-(aminomethyl)-5-bromo-3-fluoro-benzoate hydrochloride (Example 10, step 2) (379 mg, 0.888 mmol, purity=70%, 1.2 equiv.) in 3.0 ml of acetonitrile was stirred at 70° ° C. for 16 hours. Trimethylsilyl cyanide (89.9 mg, 0.113 ml, 0.888 mmol, 1.2 equiv.) was added at room temperature and the reaction mixture was stirred at 70° C. for 2 hours. Hunig's base (191 mg, 0.258 ml, 1.48 mmol, 2.0 equiv.) was added at room temperature and the reaction mixture was stirred at 70° C. for 4 hours. The reaction mixture was extracted with saturated NaHCO₃-solution and two times with ethyl acetate. The organic layers were washed with water and brine, dried over sodium sulfate and concentrated to dryness. The crude product was purified by flash chromatography on a silica gel column eluting with an ethyl acetate:heptane 0:100 to 100:0 gradient to obtain the desired (2RS)-2-(6-bromo-4-fluoro-1-oxo-isoindolin-2-yl)-2-(6,7-dihydro-5H-pyrrolizin-1-yl)acetonitrile (70 mg, 25% yield) as a yellow solid, MS: m/e=374.0/375.9 (M+H⁺).

Step 4: Sodium (2RS)-2-(6-bromo-4-fluoro-1-oxo-isoindolin-2-yl)-2-(6,7-dihydro-5H-pyrrolizin-1-yl)acetate

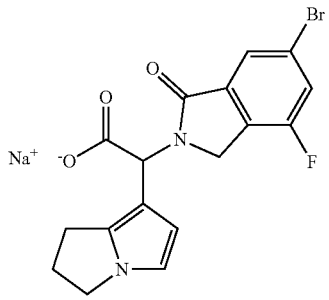

(2RS)-2-(6-Bromo-4-fluoro-1-oxo-isoindolin-2-yl)-2-(6,7-dihydro-5H-pyrrolizin-1-yl)acetonitrile (Example 10, step 3) (110 mg, 0.294 mmol) was dissolved in 1.0 ml of ethanol. NaOH (2M in water) (0.294 ml, 0.588 mmol, 2 equiv.) was added at room temperature. The mixture was stirred at 85° C. for 16 hours. The reaction mixture was cooled to room temperature and then concentrated to dryness. The desired sodium (2RS)-2-(6-bromo-4-fluoro-1-oxo-isoindolin-2-yl)-2-(6,7-dihydro-5H-pyrrolizin-1-yl)acetate (165 mg, 95% yield, 70% purity) was obtained as a yellow solid, MS: m/e=393.0/395.0 (M+H⁺) and used in the next step without further purification.

Step 5: (2RS)-2-(6-Bromo-4-fluoro-1-oxo-isoindolin-2-yl)-2-(6,7-dihydro-5H-pyrrolizin-1-yl)-N-thiazol-2-yl-acetamide

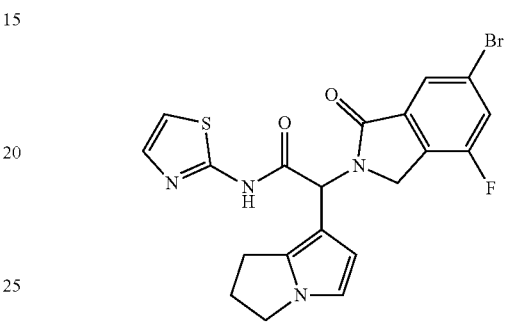

The title compound was obtained as a light brown solid, MS: m/e=474.9/476.9 (M+H⁺), using chemistry similar to that described in Example 1, step 7 starting from sodium (2RS)-2-(6-bromo-4-fluoro-1-oxo-isoindolin-2-yl)-2-(6,7-dihydro-5H-pyrrolizin-1-yl)acetate (Example 10, step 4) and thiazol-2-amine.

Step 6: (2RS)-2-(6,7-Dihydro-5H-pyrrolizin-1-yl)-2-[4-fluoro-6-[2-[4-[(4-hydroxy-1-piperidyl)methyl]phenyl]ethynyl]-1-oxo-isoindolin-2-yl]-N-thiazol-2-yl-acetamide

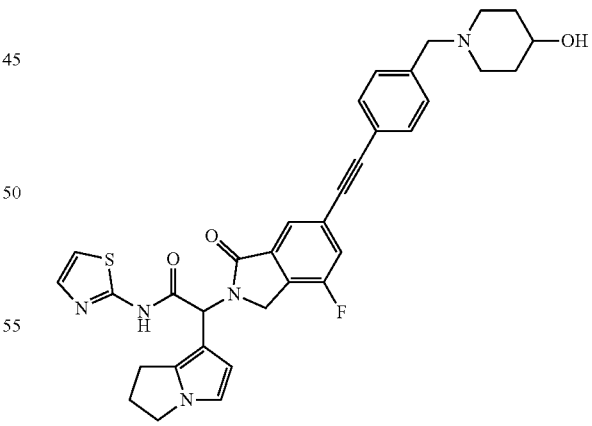

The title compound was obtained as a yellow solid, MS: m/e=610.4 (M+H⁺), using chemistry similar to that described in Example 1, step 9 starting from (2RS)-2-(6-bromo-4-fluoro-1-oxo-isoindolin-2-yl)-2-(6,7-dihydro-5H-pyrrolizin-1-yl)-N-thiazol-2-yl-acetamide (Example 10, step 5) and 1-[(4-ethynylphenyl)methyl]piperidin-4-ol (Example 9, step 1).

Example 11

(2RS)-2-[4-Chloro-6-[4-(4-hydroxy-1-piperidyl)phenyl]-1-oxo-isoindolin-2-yl]-2-(6,7-dihydro-5H-pyrrolo[1,2-c]imidazol-1-yl)-N-thiazol-2-yl-acetamide

Step 1: Ethyl (2RS)-2-[4-Chloro-6-[4-(4-hydroxy-1-piperidyl)phenyl]-1-oxo-isoindolin-2-yl]-2-(6,7-dihydro-5H-pyrrolo[1,2-c]imidazol-1-yl)acetate

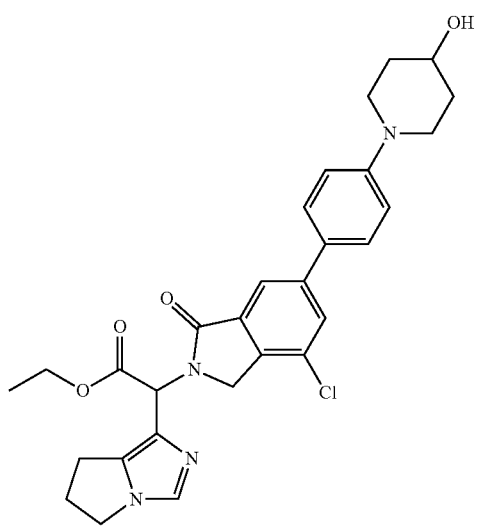

The title compound was obtained as a brown solid, MS: m/e=535.2/537.2 (M+H$^+$), using chemistry similar to that described in Example 3, step 1 starting from ethyl (2RS)-2-(4-chloro-6-iodo-1-oxo-isoindolin-2-yl)-2-(6,7-dihydro-5H-pyrrolo[1,2-c]imidazol-1-yl)acetate (Example 9, step 4) and 1-[4-(4,4,5,5-tetramethyl-1,3,2-dioxaborolan-2-yl)phenyl]piperidin-4-ol.

Step 2: (2RS)-2-[4-Chloro-6-[4-(4-hydroxy-1-piperidyl)phenyl]-1-oxo-isoindolin-2-yl]-2-(6,7-dihydro-5H-pyrrolo[1,2-c]imidazol-1-yl)-N-thiazol-2-yl-acetamide

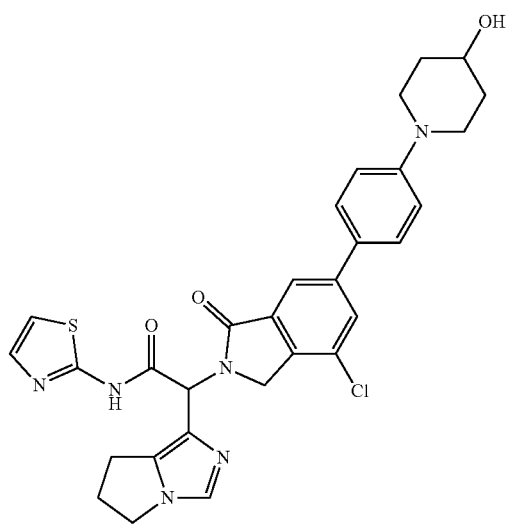

The title compound was obtained as a white solid, MS: m/e=589.2/591.2 (M+H$^+$), using chemistry similar to that described in Example 3, step 2 starting from ethyl (2RS)-2-[4-chloro-6-[4-(4-hydroxy-1-piperidyl)phenyl]-1-oxo-isoindolin-2-yl]-2-(6,7-dihydro-5H-pyrrolo[1,2-c]imidazol-1-yl)acetate (Example 11, step 1) and thiazol-2-amine.

Example 12

(2RS)-2-(6,7-Dihydro-5H-pyrrolo[1,2-c]imidazol-1-yl)-2-[4-fluoro-6-[2-[4-(hydroxymethyl)phenyl]ethynyl]-1-oxo-isoindolin-2-yl]-N-thiazol-2-yl-acetamide The title compound was obtained as a light yellow solid, MS: m/e=526.1 (M+H$^+$), using chemistry similar to that described in Example 1, step 9 starting from (2RS)-2-(6-Bromo-4-fluoro-1-oxo-isoindolin-2-yl)-2-(6,7-dihydro-5H-pyrrolo[1,2-c]imidazol-1-yl)-N-thiazol-2-yl-acetamide (Example 1, step 8) and (4-ethynylphenyl)methanol.

Example 13

(2RS)-2-[7-chloro-4-fluoro-6-[2-[4-[(4-hydroxy-1-piperidyl)methyl]phenyl]ethynyl]-1-oxo-isoindolin-2-yl]-2-(6,7-dihydro-5H-pyrrolo[1,2-c]imidazol-1-yl)-N-thiazol-2-yl-acetamide

Step 1: 2-Chloro-3-iodo-6-methyl-5-nitrobenzoic acid

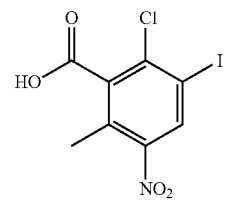

6-Chloro-2-methyl-3-nitrobenzoic acid (3.8 g, 15.9 mmol) was dissolved in 18 ml of sulfuric acid. 1,3-Diiodo-5,5-dimethylimidazolidine-2,4-dione (6.9 g, 18.2 mmol, 1.15 equiv.) was added at room temperature. The mixture was stirred at room temperature for 16 hours. The reaction mixture was poured onto water and the resulting precipitate filtered off. The solid was dried to obtain the desired 2-chloro-3-iodo-6-methyl-5-nitrobenzoic acid (5.37 g, quant. yield) as a brown foam, MS: m/e=339.8/341.7 (M+H$^+$).

Step 2: Methyl 2-chloro-3-iodo-6-methyl-5-nitrobenzoate

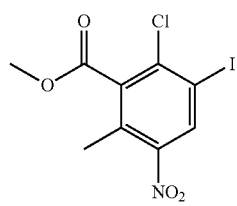 [SMILES: COC(=O)c1c(C)c([N+](=O)[O-])cc(I)c1Cl]

2-Chloro-3-iodo-6-methyl-5-nitrobenzoic acid (Example 13, step 1) (5.37 g, 14.2 mmol) was dissolved in 25 ml of DMF. Potassium carbonate (3.9 g, 28.3 mmol, 2 equiv.) and iodomethane (2.1 g, 14.9 mmol, 1.05 equiv.) were added at room temperature. The mixture was stirred at room temperature for 2 hours. The reaction mixture was extracted with saturated sodiumbicarbonate solution and two times with ethyl acetate. The organic layers were extracted with water and 10% lithium chloride solution. The organic layers were combined, dried over sodium sulfate and concentrated to dryness. The crude product was purified by flash chromatography on a silica gel column eluting with a heptane:ethyl acetate 100:0 to 60:40 gradient to obtain the desired methyl 2-chloro-3-iodo-6-methyl-5-nitrobenzoate (2.89 g, 57% yield) as a lightly yellow solid, MS: m/e=353.9/355.9 (M+H$^+$).

Step 3: Methyl 3-amino-6-chloro-5-iodo-2-methylbenzoate

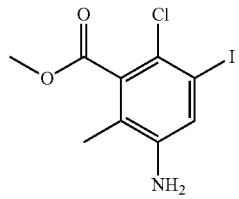

Methyl 2-chloro-3-iodo-6-methyl-5-nitrobenzoate (Example 13, step 2) (2.89 g, 8.13 mmol) was dissolved in 30 ml of methanol and 15 ml of water. Ammonium chloride (4.35 g, 81.3 mmol, 10 equiv.) and iron (2.72 g, 48.8 mmol, 6 equiv.) were added at room temperature. The mixture was stirred at 70° C. for 16 hours. The reaction mixture was filtered and evaporated to dryness. The residue was extracted with saturated sodiumbicarbonate solution and two times with ethyl acetate. The organic layers were extracted with water and brine. The organic layers were combined, dried over sodium sulfate and concentrated to dryness. The crude product was purified by flash chromatography on a silica gel column eluting with a heptane:ethyl acetate 100:0 to 30:70 gradient to obtain the desired methyl 3-amino-6-chloro-5-iodo-2-methylbenzoate (1.9 g, 72% yield) as an orange oil, MS: m/e=324.9/326.9 (M+H$^+$).

Step 4: Methyl 2-chloro-5-fluoro-3-iodo-6-methylbenzoate (696 mg, 2.12 mmol, 49.1% Yield)

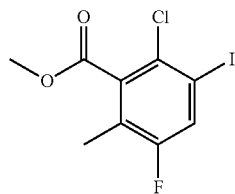

Methyl 3-amino-6-chloro-5-iodo-2-methylbenzoate (Example 13, step 3) (1.4 g, 4.3 mmol) was dissolved in 10 ml of dioxane. Nitrosonium tetrafluoroborate (0.55 g, 4.74 mmol, 1.1 equiv.) was added in portion and under ice cooling at room temperature. The mixture was stirred at room temperature for 30 minutes and at 110° C. for 90 minutes. The reaction mixture was poured onto water and extracted twice with ethyl acetate. The organic layers were extracted with brine, dried over sodium sulfate and concentrated to dryness. The crude product was purified by flash chromatography on a silica gel column eluting with a heptane:ethyl acetate 100:0 to 75:25 gradient to obtain the desired methyl 2-chloro-5-fluoro-3-iodo-6-methylbenzoate (696 mg, 49% yield) as a colorless oil, MS: m/e=327.1/329.1 (M−H$^+$).

Step 5: Methyl 2-(bromomethyl)-6-chloro-3-fluoro-5-iodobenzoate

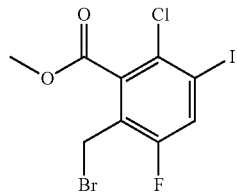

The title compound was obtained as a colorless solid, MS: m/e=409.0 (M+H$^+$), using chemistry similar to that described in Example 1, step 5 starting from methyl 2-chloro-5-fluoro-3-iodo-6-methylbenzoate (Example 13, step 4).

Step 6: Ethyl (2RS)-2-(7-chloro-4-fluoro-6-iodo-1-oxo-isoindolin-2-yl)-2-(6,7-dihydro-5H-pyrrolo[1,2-c]imidazol-1-yl)acetate

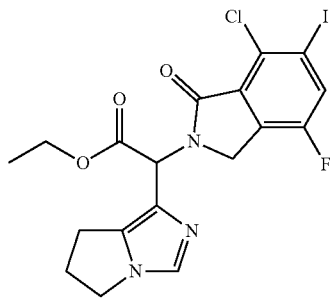 [SMILES: CCOC(=O)C(c1ncn2c1CCC2)N1Cc2c(F)cc(I)c(Cl)c2C1=O]

The title compound was obtained as a brown solid, MS: m/e=504.1/506.1 (M+H$^+$), using chemistry similar to that described in Example 1, step 6 starting from ethyl (2RS)-2-amino-2-(6,7-dihydro-5H-pyrrolo[1,2-c]imidazol-1-yl)acetate hydrochloride (Example 1, step 4) and methyl 2-(bromomethyl)-6-chloro-3-fluoro-5-iodobenzoate (Example 13, step 5).

Step 7: (2RS)-2-(7-Chloro-4-fluoro-6-iodo-1-oxo-isoindolin-2-yl)-2-(6,7-dihydro-5H-pyrrolo[1,2-c]imidazol-1-yl)-N-thiazol-2-yl-acetamide

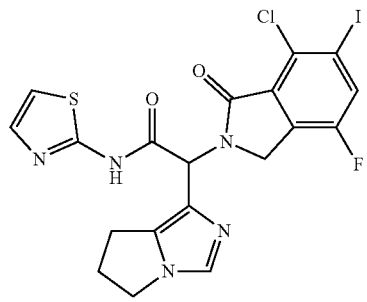 [SMILES: O=C(Nc1nccs1)C(c1ncn2c1CCC2)N1Cc2c(F)cc(I)c(Cl)c2C1=O]

The title compound was obtained as a light yellow solid, MS: m/e=558.1/560.1 (M+H⁺), using chemistry similar to that described in Example 3, step 2 starting from ethyl (2RS)-2-(7-chloro-4-fluoro-6-iodo-1-oxo-isoindolin-2-yl)-2-(6,7-dihydro-5H-pyrrolo[1,2-c]imidazol-1-yl)acetate (Example 13, step 6) and thiazol-2-amine.

Step 8: (2RS)-2-[7-Chloro-4-fluoro-6-[2-[4-[(4-hydroxy-1-piperidyl)methyl]phenyl]ethynyl]-1-oxo-isoindolin-2-yl]-2-(6,7-dihydro-5H-pyrrolo[1,2-c]imidazol-1-yl)-N-thiazol-2-yl-acetamide

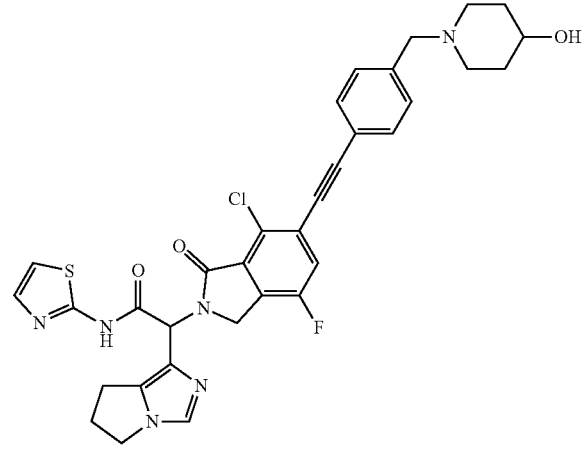 [SMILES: O=C(Nc1nccs1)C(c1ncn2c1CCC2)N1Cc2c(F)cc(C#Cc3ccc(CN4CCC(O)CC4)cc3)c(Cl)c2C1=O]

The title compound was obtained as a light brown solid, MS: m/e=645.3/647.3 (M+H⁺), using chemistry similar to that described in Example 1, step 9 starting from (2RS)-2-(7-chloro-4-fluoro-6-iodo-1-oxo-isoindolin-2-yl)-2-(6,7-dihydro-5H-pyrrolo[1,2-c]imidazol-1-yl)-N-thiazol-2-yl-acetamide (Example 13, step 7) and 1-[(4-ethynylphenyl)methyl]piperidin-4-ol (Example 9, step 1).

Example 14

(2RS)-2-(6,7-Dihydro-5H-pyrrolo[1,2-c]imidazol-1-yl)-2-[4-fluoro-1-oxo-6-[2-[4-(1-piperidylmethyl)phenyl]ethynyl]isoindolin-2-yl]-N-thiazol-2-yl-acetamide The title compound was obtained as a light yellow semi-solid, MS: m/e=595.4 (M+H⁺), using chemistry similar to that described in Example 1, step 10 starting from (2RS)-2-(6,7-dihydro-5H-pyrrolo[1,2-c]imidazol-1-yl)-2-[4-fluoro-6-[2-(4-formylphenyl)ethynyl]-1-oxo-isoindolin-2-yl]-N-thiazol-2-yl-acetamide (Example 1, step 9) and piperidine.

We claim:
1. A compound of formula I,

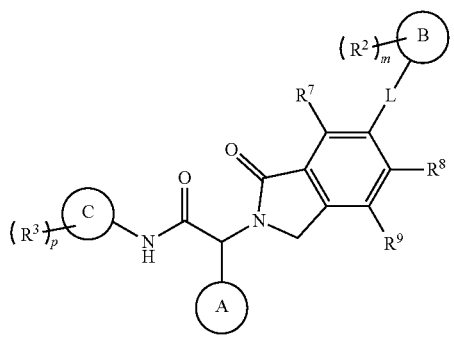

wherein
L is absent or —(C≡C)—,
A is

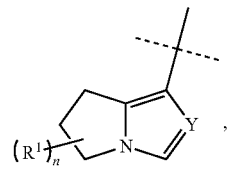

B is aryl or heteroaryl,
C is heteroaryl,
Y is N, C(OH) or CH,
$R^1$ is each independently selected from the group consisting of
 i) amino,
 ii) $C_{1-6}$-alkyl,
 iii) $C_{1-6}$-alkoxy,
 iv) cyano,
 v) halogen,
 vi) halogen-$C_{1-6}$-alkyl,
 vii) halogen-$C_{1-6}$-alkoxy, and
 viii) hydroxy;
$R^2$ is each independently selected from the group consisting of
 i) —(CH₂)$_k$—N($R^4$, $R^5$),
 ii) —(C=O)—N($R^4$, $R^5$),
 iii) halogen,
 iv) halogen-$C_{1-6}$-alkyl,
 v) —NH—(C=O)—$C_{1-6}$-alkyl, and
 vi) $C_{1-6}$-alkyl, optionally substituted by OH;
$R^3$ is each independently selected from the group consisting of
 i) amino,
 ii) $C_{1-6}$-alkyl,
 iii) $C_{1-6}$-alkoxy,
 iv) cyano,
 v) halogen, vi) halogen-$C_{1-6}$-alkyl,
vii) halogen-$C_{1-6}$-alkoxy, and
viii) hydroxy;
$R^4$ is each independently selected from the group consisting of
i) H, and
ii) $C_{1-6}$-alkyl;
$R^5$ is each independently selected from the group consisting of
i) H,
ii) $C_{1-6}$-alkyl, and
iii) —(C=O)—$C_{1-6}$-alkyl;
or $R^4$ and $R^5$ form together with the N they are attached to a heterocyclyl, which heterocyclyl is optionally substituted by one to three $R^6$;
$R^6$ is each independently selected from the group consisting of
i) —OH,
ii) halogen,
iii) $C_{3-8}$-cycloalkyl,
iv) halogen-$C_{1-6}$-alkyl,
v) $C_{1-6}$-alkoxy-$C_{1-6}$-alkyl,
vi) cyano-$C_{1-6}$-alkyl,
vii) $C_{1-6}$-alkyl, and
viii) —(C=O)—$C_{1-6}$-alkyl;
$R^7$ is each independently selected from the group consisting of
i) H,
ii) halogen,
iii) halogen-$C_{1-6}$-alkoxy,
iv) $C_{1-6}$-alkoxy, and
v) $C_{1-6}$-alkyl;
$R^8$ is each independently selected from the group consisting of
i) H,
ii) halogen,
iii) $C_{1-6}$-alkoxy, and
iv) $C_{1-6}$-alkyl;
$R^9$ is each independently selected from the group consisting of
i) H,
ii) halogen,
iii) halogen-$C_{1-6}$-alkoxy,
iv) $C_{1-6}$-alkoxy, and
v) $C_{1-6}$-alkyl;
k is 0, 1 or 2;
n is 0, 1, 2, 3 or 4;
m is 0, 1 or 2;
p is 0 or 1;
or a pharmaceutically acceptable salt thereof.

2. The compound of claim 1 or a pharmaceutically acceptable salt thereof, wherein
L is absent or —(C≡C)—,
A is

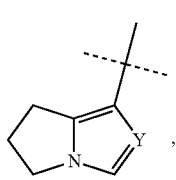

B is aryl or heteroaryl,
C is heteroaryl,
Y is N or CH, $R^2$ is each independently selected from the group consisting of
i) —$(CH_2)_k$—$N(R^4, R^5)$,
ii) halogen-$C_{1-6}$-alkyl, and
iii) $C_{1-6}$-alkyl, optionally substituted by OH;
$R^4$ and $R^5$ form together with the N they are attached to a heterocyclyl, which heterocyclyl is optionally substituted by one to three $R^6$;
$R^6$ is each independently selected from the group consisting of
i) —OH,
ii) halogen,
iii) $C_{3-8}$-cycloalkyl,
iv) halogen-$C_{1-6}$-alkyl,
v) $C_{1-6}$-alkoxy-$C_{1-6}$-alkyl,
vi) cyano-$C_{1-6}$-alkyl, and
vii) $C_{1-6}$-alkyl;
$R^7$ is H or halogen;
$R^8$ is H;
$R^9$ is halogen;
k is 0 or 1;
n is 0;
m is 1;
p is 0.

3. The compound of claim 1 or a pharmaceutically acceptable salt thereof, wherein A is

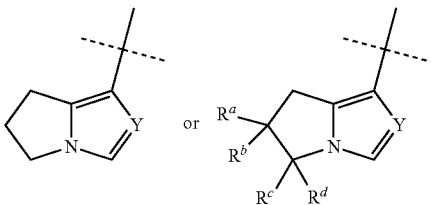

wherein
Y is N or CH, and
$R^a$, $R^b$, $R^c$ or $R^d$ is each independently selected from the group consisting of
i) H,
ii) amino,
iii) $C_{1-6}$-alkyl,
iv) $C_{1-6}$-alkoxy,
v) cyano,
vi) halogen,
vii) halogen-$C_{1-6}$-alkyl,
viii) halogen-$C_{1-6}$-alkoxy, and
ix) hydroxyl.

4. The compound of claim 1, or a pharmaceutically acceptable salt thereof, wherein A is

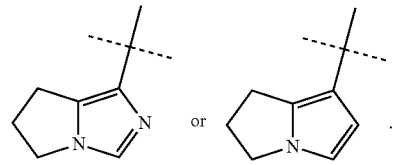

5. The compound of claim 1, or a pharmaceutically acceptable salt thereof, wherein B is aryl.

6. The compound of claim 1, or a pharmaceutically acceptable salt thereof, wherein B is phenyl.

7. The compound of claim 1, or a pharmaceutically acceptable salt thereof, wherein B is heteroaryl.

8. The compound of claim 1, or a pharmaceutically acceptable salt thereof, wherein B is pyridinyl.

9. The compound of claim 1, or a pharmaceutically acceptable salt thereof, wherein C is pyridinyl.

10. The compound of claim 1, or a pharmaceutically acceptable salt thereof, wherein C is thiazolyl.

11. The compound of claim 1, or a pharmaceutically acceptable salt thereof, wherein n is 0.

12. The compound of claim 1, or a pharmaceutically acceptable salt thereof, wherein m is 1.

13. The compound of claim 1, or a pharmaceutically acceptable salt thereof, wherein p is 0.

14. The compound of claim 1, or a pharmaceutically acceptable salt thereof, wherein $R^2$ is —$(CH_2)_k$—$N(R^4, R^5)$, k is 0 or 1 and $R^4$ and $R^5$ form together with the N they are attached to a heterocyclyl, which heterocyclyl is optionally substituted by $R^6$.

15. The compound of claim 1, or a pharmaceutically acceptable salt thereof, wherein $R^2$ is —$(CH_2)_k$—$N(R^4, R^5)$, k is 0 or 1 and $R^4$ and $R^5$ form together with the N they are attached to piperazinyl, piperidinyl or morpholino, which piperazinyl, piperidinyl or morpholino are optionally substituted by $R^6$.

16. The compound of claim 1, or a pharmaceutically acceptable salt thereof, selected from the group consisting of

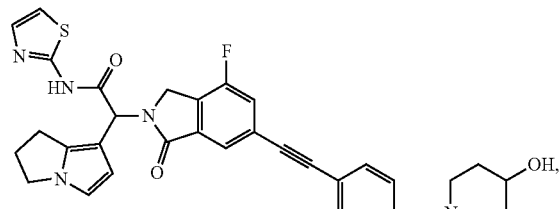

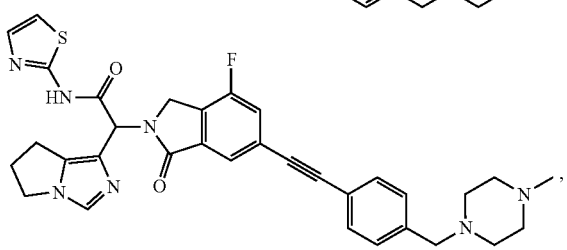

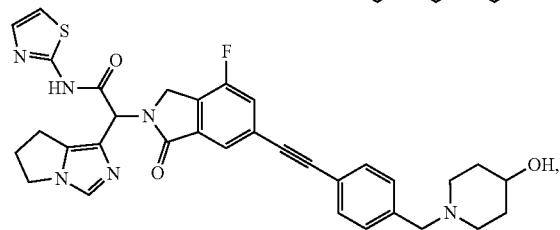

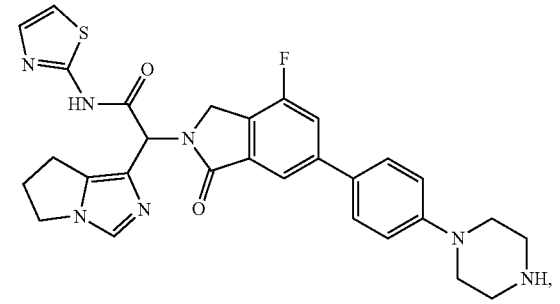

-continued

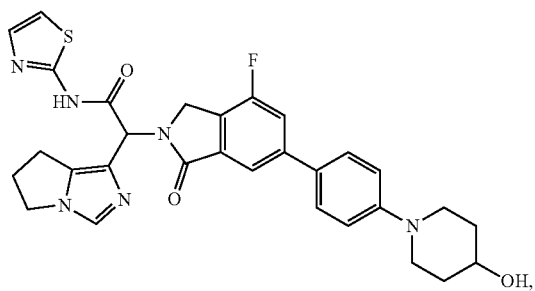

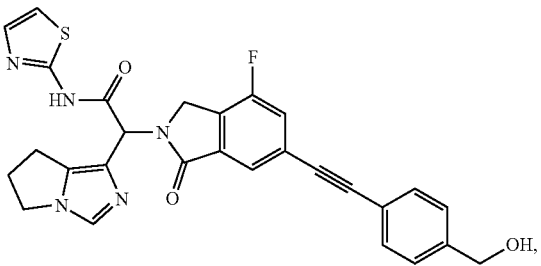

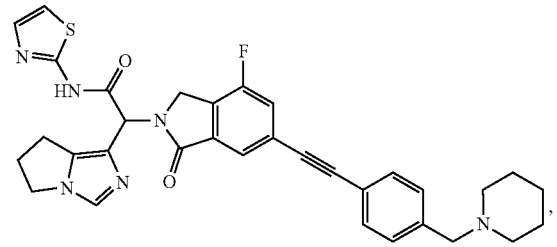

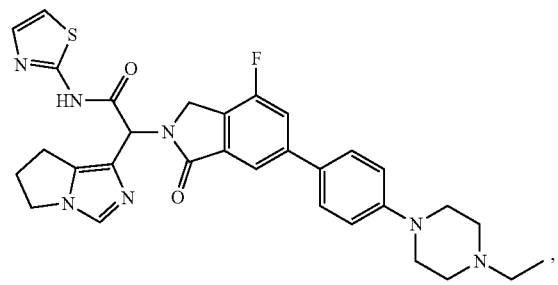

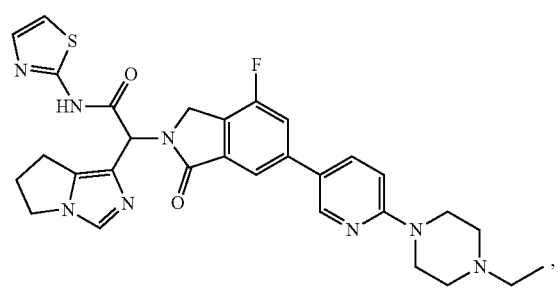

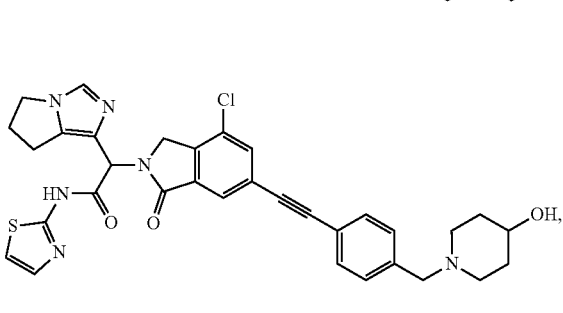

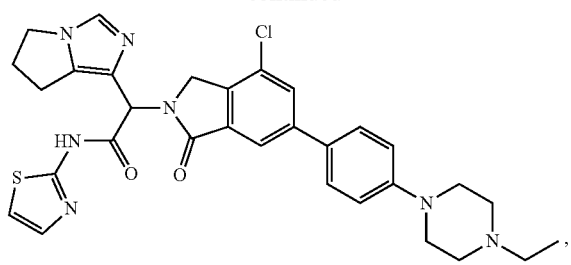
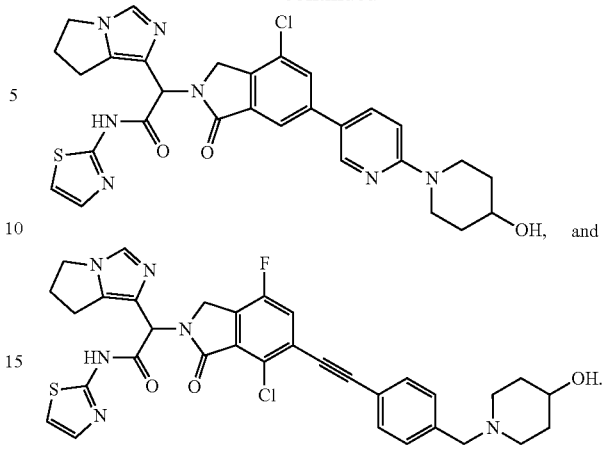
17. The compound of claim 1, or a pharmaceutically acceptable salt thereof, that is selected from the group consisting of
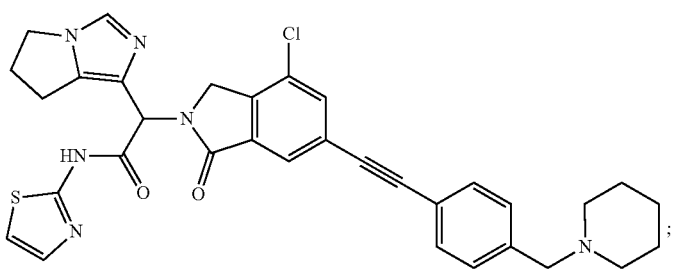
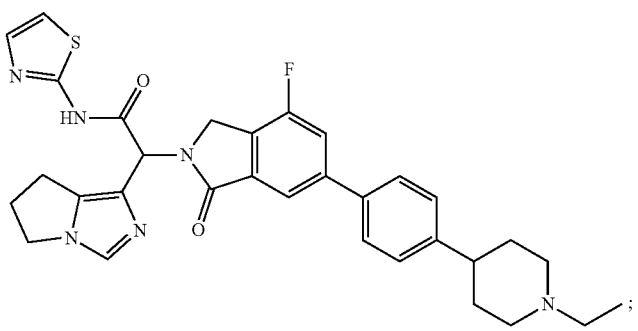
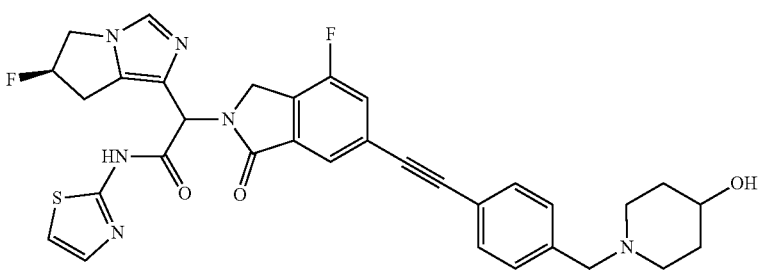

-continued
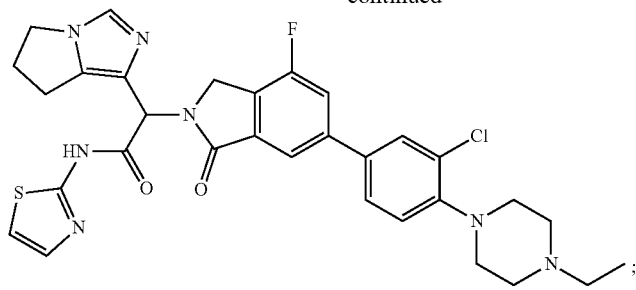
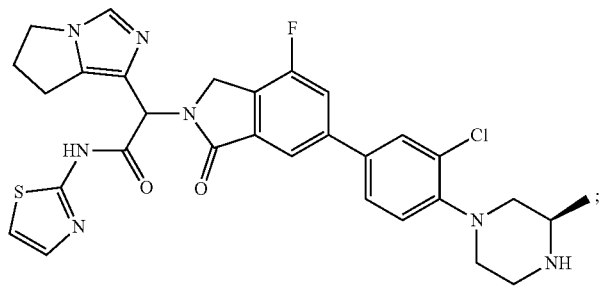
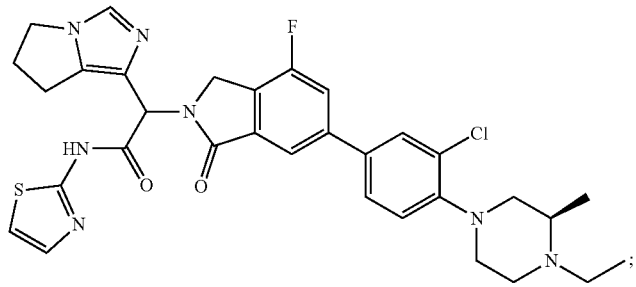
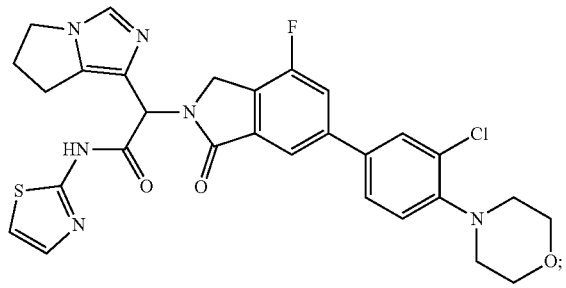
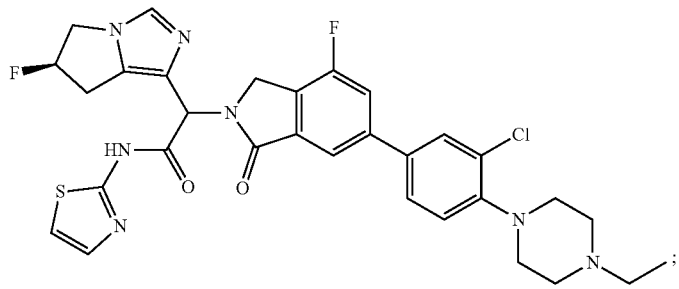
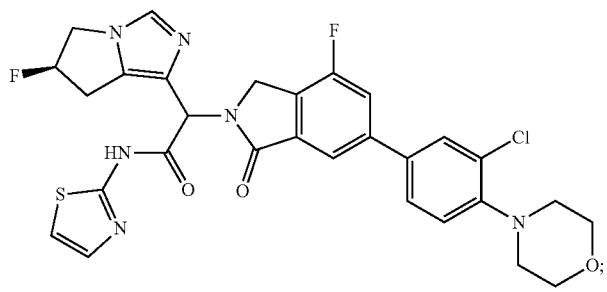

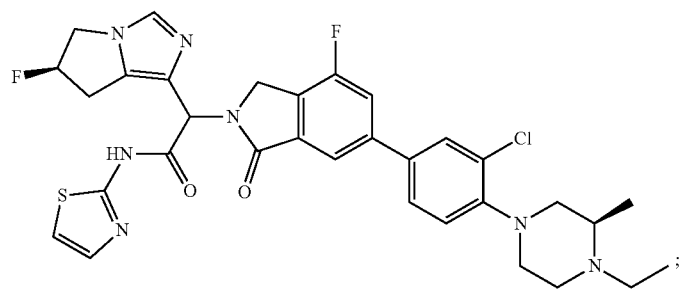
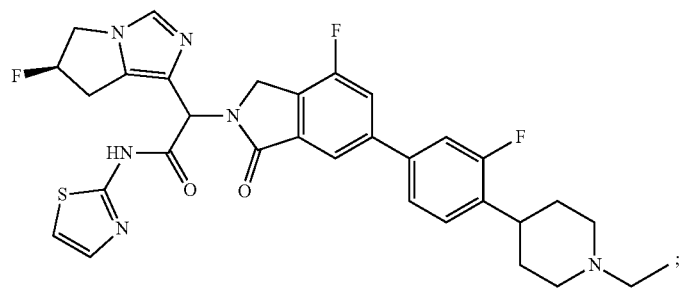
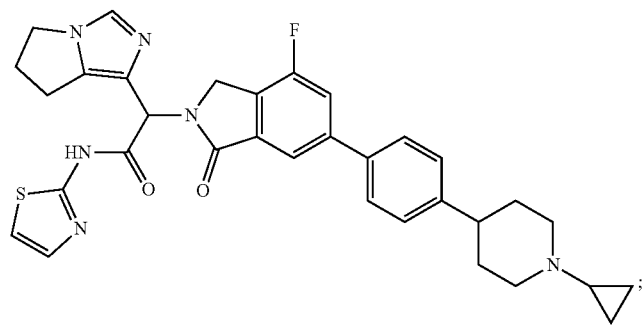
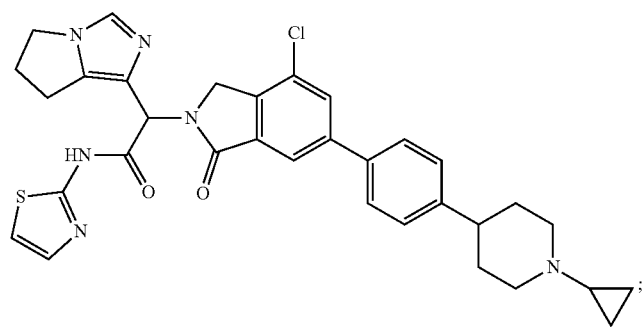
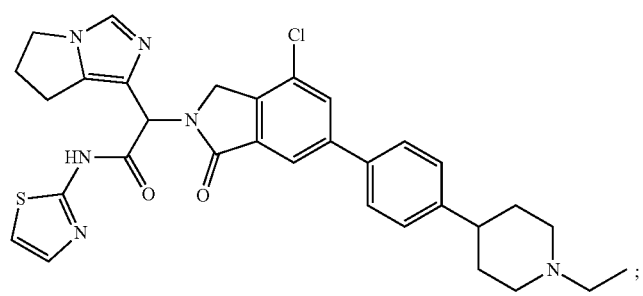

-continued
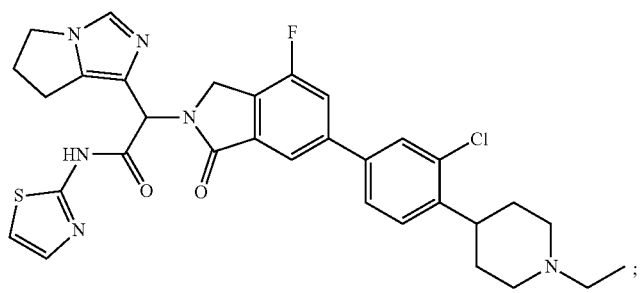
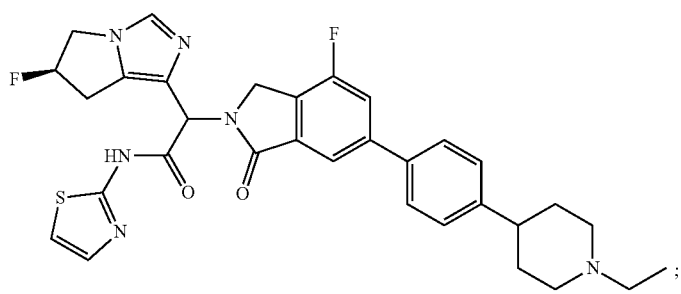
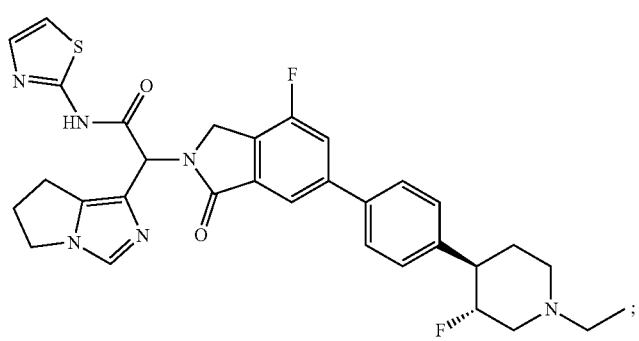
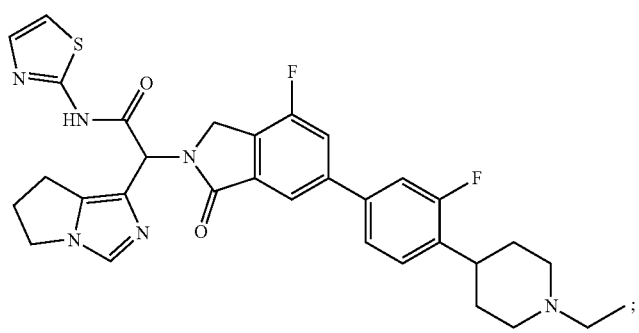
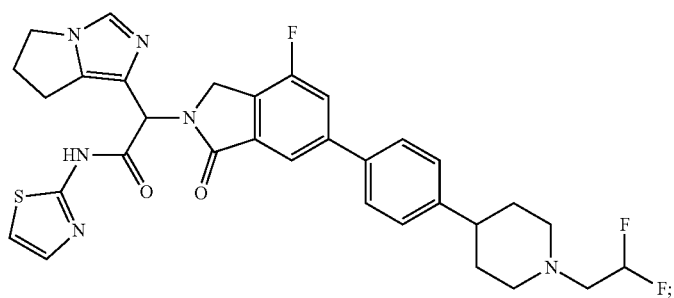

-continued
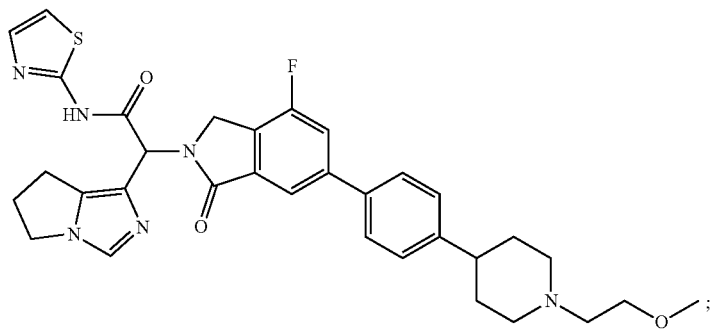
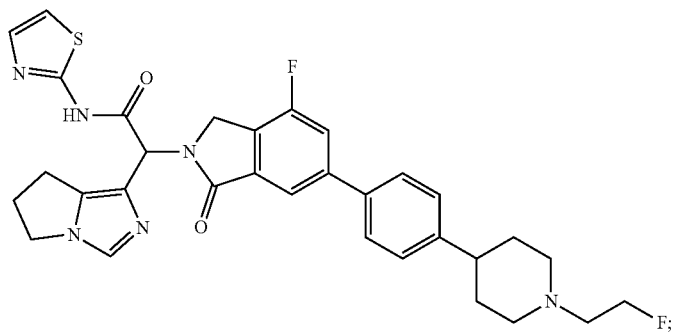
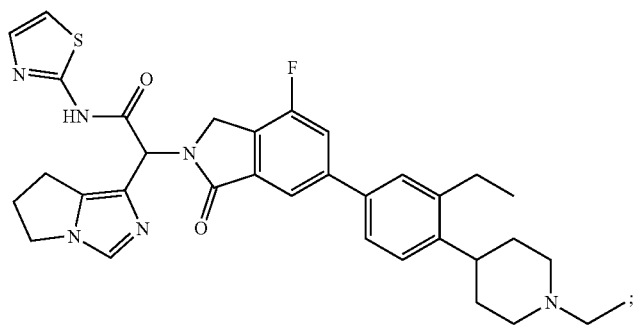
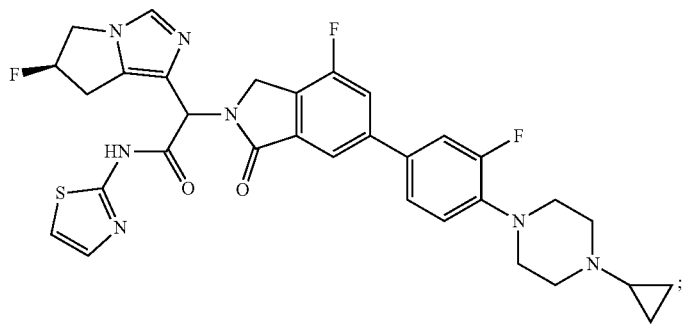
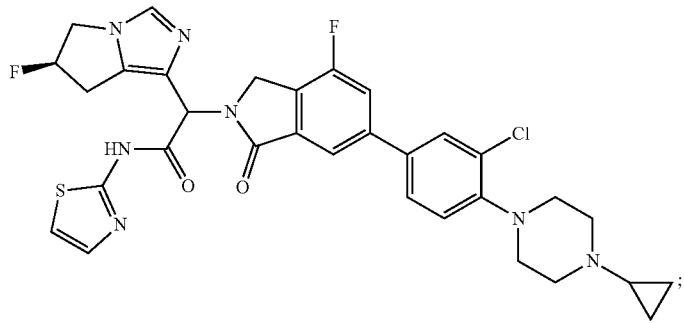

-continued
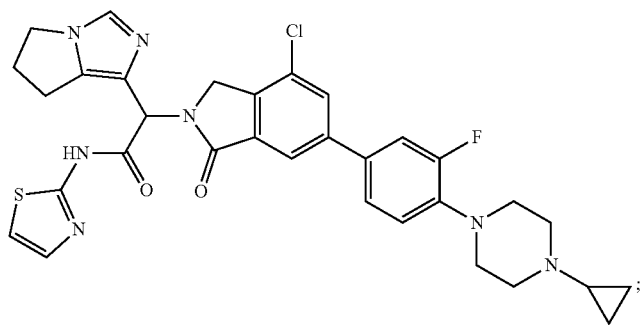
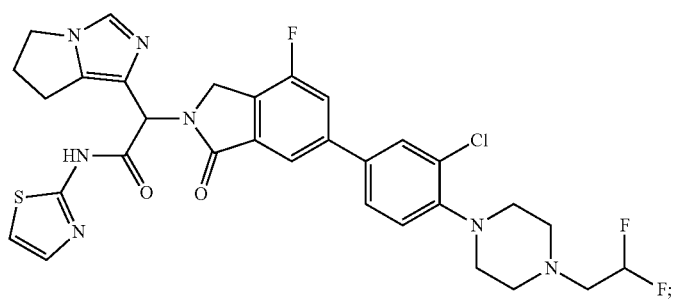
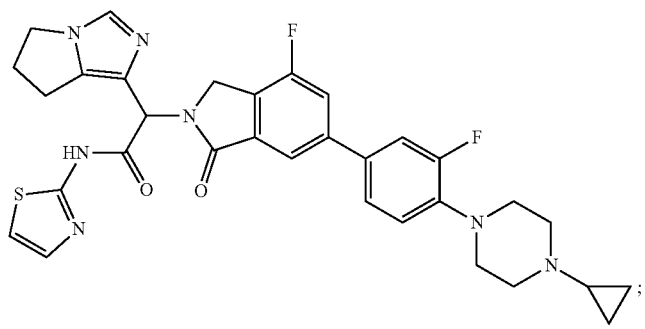
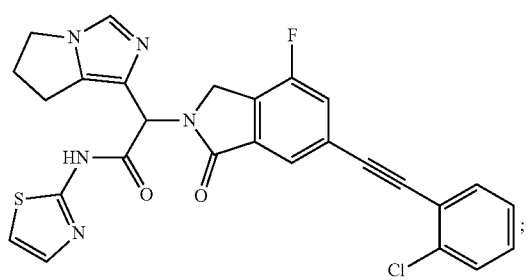
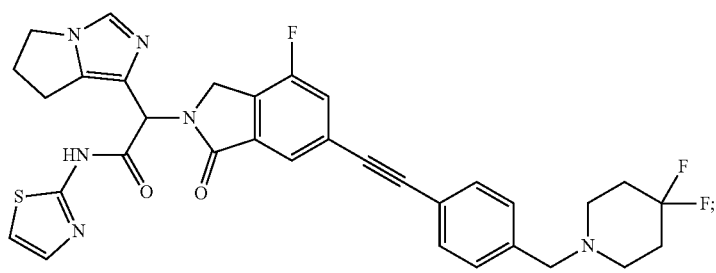

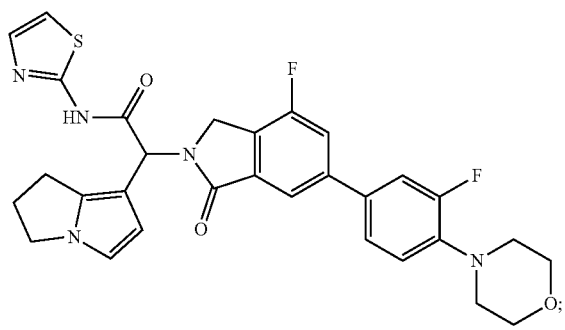
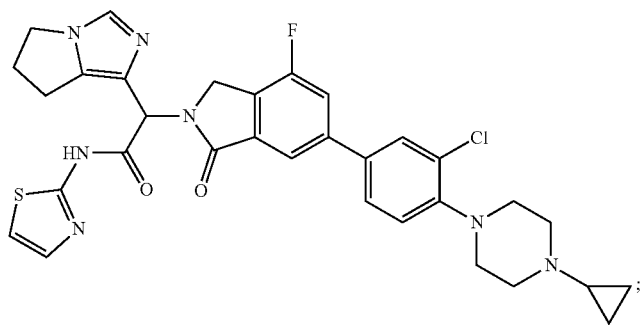
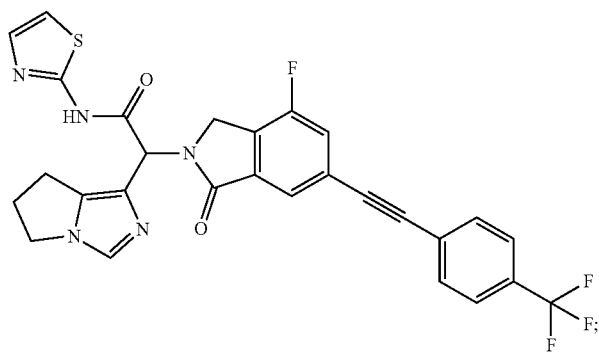
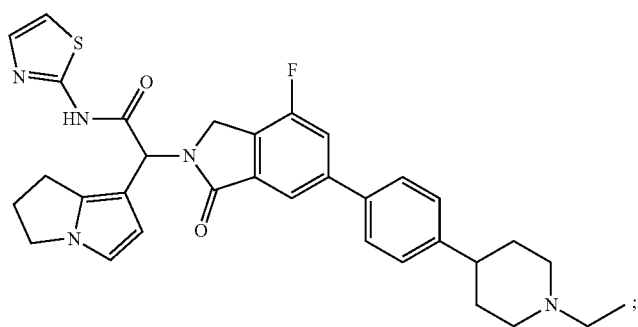
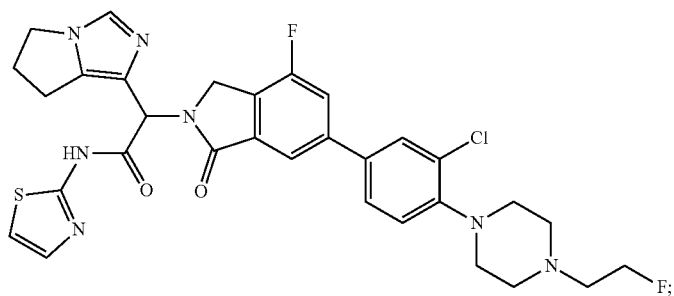

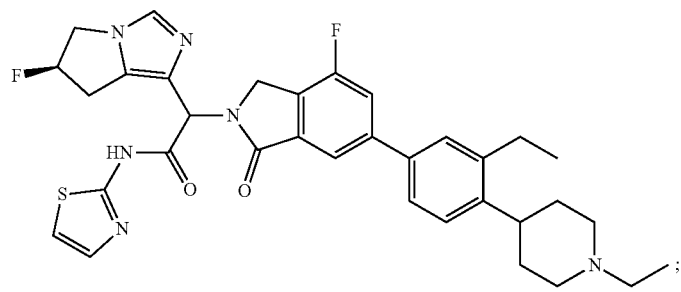
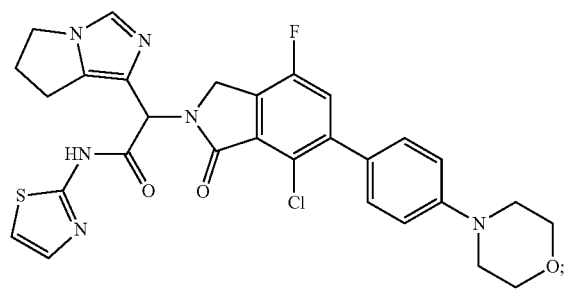
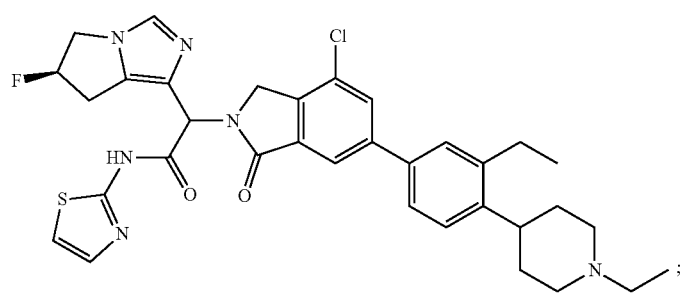
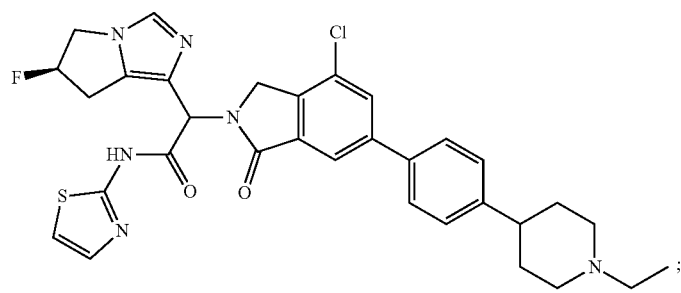
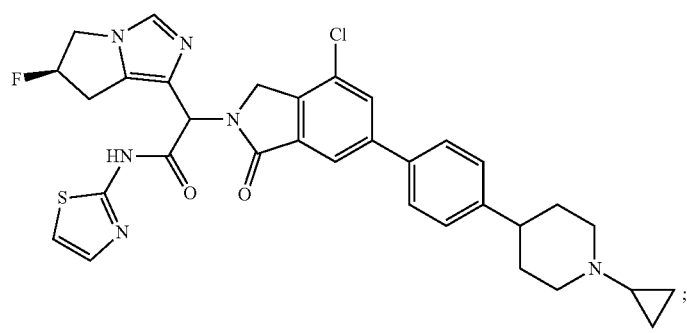

-continued
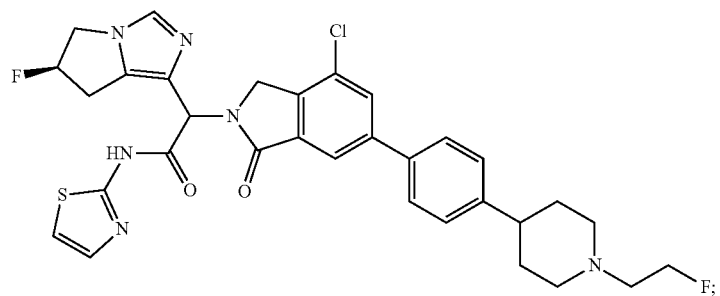
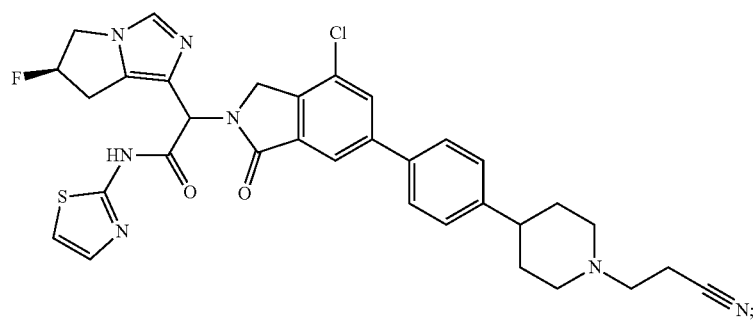
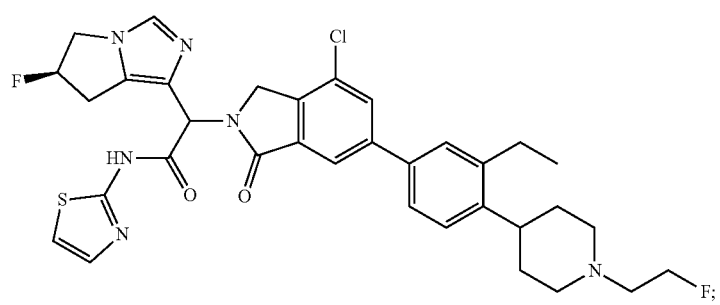
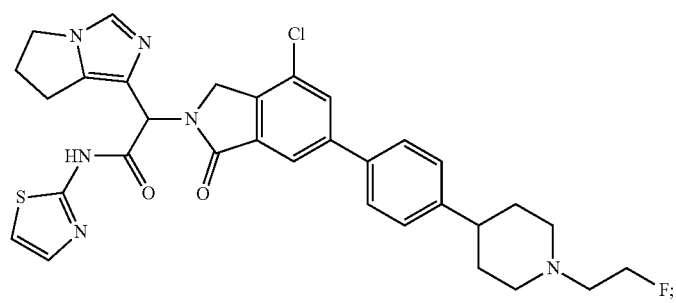
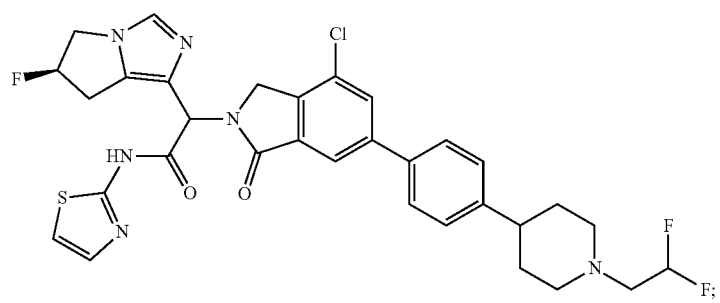

-continued
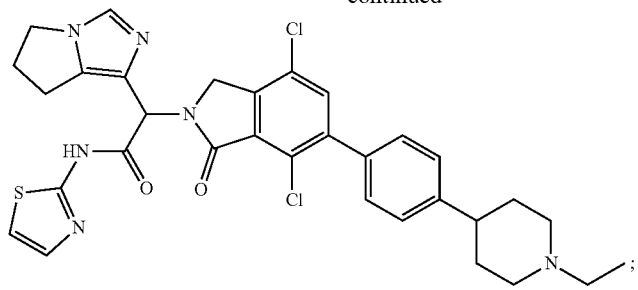
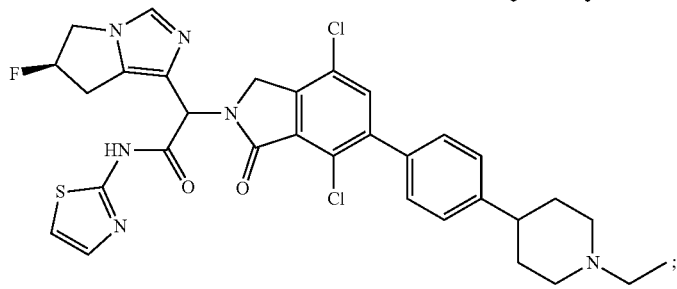
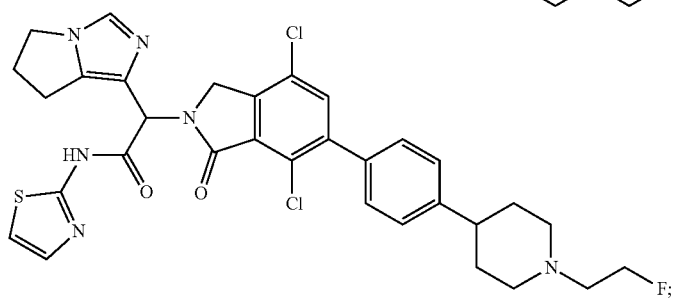
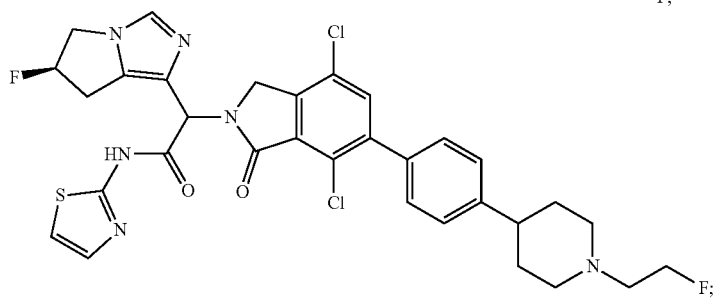
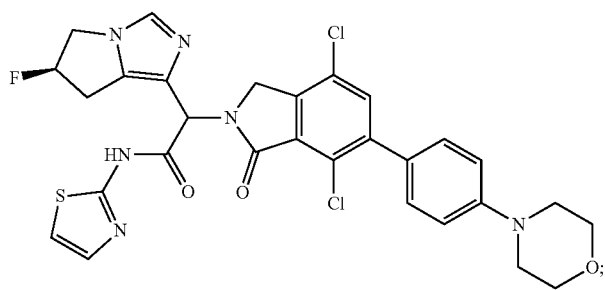
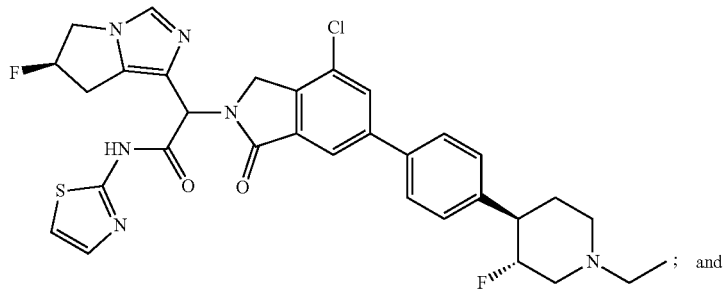

-continued

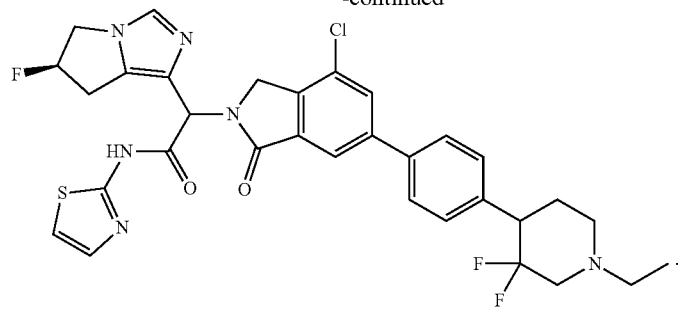

18. The compound of claim 1, or a pharmaceutically acceptable salt thereof, according to claim 1, that is selected from the group consisting of

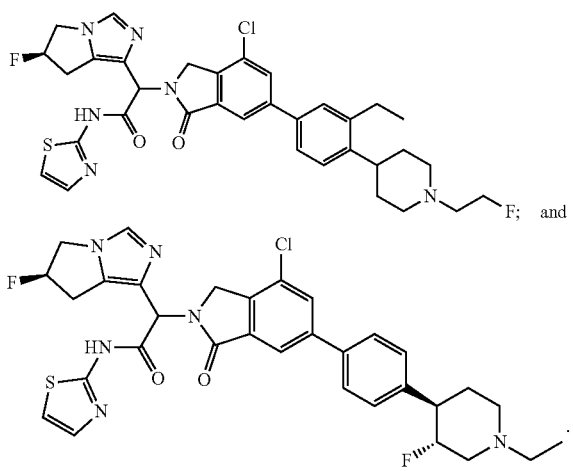

19. A method of treating a disorder mediated by the epidermal growth factor receptor (EGFR) comprising administering a compound of claim 1, or a pharmaceutically acceptable salt thereof, to a patient in need thereof.

20. The method of claim 19, wherein the patient is a human.
21. The method of claim 20, wherein the disorder is cancer.
22. The method of claim 21, wherein the cancer is non-small-cell lung cancer.
23. A pharmaceutical composition comprising a compound of claim 1, or a pharmaceutically acceptable salt thereof, and a pharmaceutically acceptable auxiliary substance.
24. The compound of claim 6, wherein L is absent.
25. The compound of claim 24, wherein $R^9$ is F.
26. The compound of claim 25, wherein A is

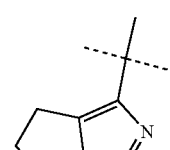

27. The compound of claim 26, wherein C is thiazolyl.
28. The compound of claim 27, wherein $R^7$ and $R^8$ are H.
29. The compound of claim 28, wherein p is 0.
30. The compound of claim 29, wherein m is 1.

* * * * *